United States Patent
Chaux et al.

(10) Patent No.: US 6,426,217 B1
(45) Date of Patent: Jul. 30, 2002

(54) MAGE-3 PEPTIDES PRESENTED BY HLA CLASS II MOLECULES

(75) Inventors: Pascal Chaux; Vincent Stroobant; Thierry Boon-Falleur; Pierre van der Bruggen; Kris Thielemans; Jurgen Kurthals, all of Brussels (BE)

(73) Assignees: Ludwig Institute for Cancer Research, New York, NY (US); Vrije Universiteit Brussel, Brussels (BE)

( * ) Notice: Subject to any disclaimer, the term of this patent is extended or adjusted under 35 U.S.C. 154(b) by 0 days.

(21) Appl. No.: 09/697,884

(22) Filed: Oct. 27, 2000

Related U.S. Application Data

(63) Continuation of application No. 09/166,448, filed on Oct. 5, 1998, now Pat. No. 6,291,430, which is a continuation-in-part of application No. 08/928,615, filed on Sep. 12, 1997, now Pat. No. 5,965,535.

(51) Int. Cl.[7] .............................. C12N 1/00; C12N 5/00; C12N 5/16; C12N 1/20; C07K 4/00

(52) U.S. Cl. ..................... 435/320.1; 435/243; 435/325; 435/326; 435/252.1; 435/334; 530/300; 530/326; 536/23.1

(58) Field of Search .......................... 536/23.1; 530/300; 530/326; 435/325, 326, 334, 243, 252.1, 320.1

(56) References Cited

U.S. PATENT DOCUMENTS

| | | |
|---|---|---|
| 5,342,774 A | 8/1994 | Boon et al. |
| 5,405,940 A | 4/1995 | Boon et al. |
| 5,585,461 A | 12/1996 | Townsend et al. |
| 5,591,430 A | 1/1997 | Townsend et al. |
| 5,965,535 A | 10/1999 | Chaux et al. |

FOREIGN PATENT DOCUMENTS

| | | |
|---|---|---|
| WO | PCT/US92/04354 | 11/1992 |
| WO | WO 94/20127 | 9/1994 |
| WO | WO 94/23031 | 10/1994 |
| WO | PCT/US95/03657 | 9/1995 |
| WO | WO 98/04582 | 2/1998 |
| WO | WO 99/14326 | 3/1999 |
| WO | WO 99/45954 | 9/1999 |

OTHER PUBLICATIONS

De Plaen et al., *Immunogenetics* 40:360–369 (1994).
Traversari et al., *Immunogenetics* 35:1643 (1991).
van der Bruggen et al., *Science* 254:1643 (1991).
Topalian, *Curr. Opin. Immunol*, 6:741–745 (1994).
Yee et al., *J. Immunol.*, 157:4079–4086 (1996).
Topalian et al., *J. Exp. Med* 183:1965–1971 (1996).
Sanderson et al., *Proc. Nat'l. Acad. Sci. USA* 92:7217–7221 (1995).
Wu et al., *Proc Nat'l Acad Sci USA* 92: 11671–11675 (1995).
Gaugler et al., *J. Exp. Med.* 179:921–930 (1994).
van der Bruggen et al., *Eur. J. Immunol.*, 24:3038–3043 (1994).
Herman et al., *Immunogenetics*, 43:377–383 (1996).
Engelhard, *Annu. Rev. Immunol.*, 12:181–207 (1994).
Chicz et al., *J. Exp. Med.*, 178:27–47 (1993).
Spatola, A.F., *Chem. and Biochem. of Amino Acids, Peptides, and Proteins* 7:267–357.
Chaux et al., *J. of Exp. Med.* 189(5):767–777, Mar. 1, 1999.

*Primary Examiner*—Geetha P. Bansal
*Assistant Examiner*—Christopher Yaen
(74) *Attorney, Agent, or Firm*—Wolf, Greenfield & Sacks, P.C.

(57) ABSTRACT

The invention describes HLA class II binding peptides encoded by the MAGE-3 tumor associated gene, as well as nucleic acids encoding such peptides and antibodies relating thereto. The peptides stimulate the activity and proliferation of $CD4^+$ T lymphocytes. Methods and products also are provided for diagnosing and treating conditions characterized by expression of the MAGE-3 gene.

16 Claims, 13 Drawing Sheets

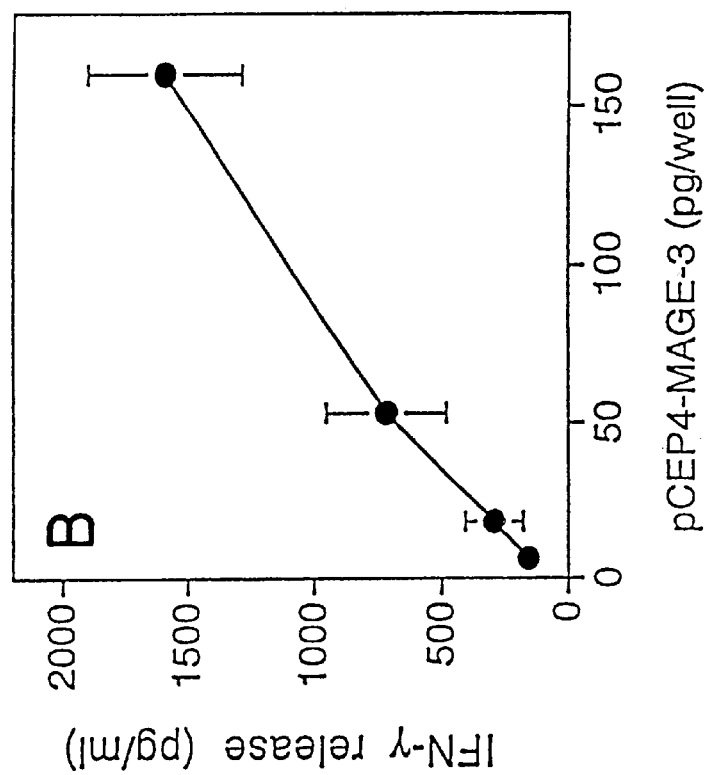
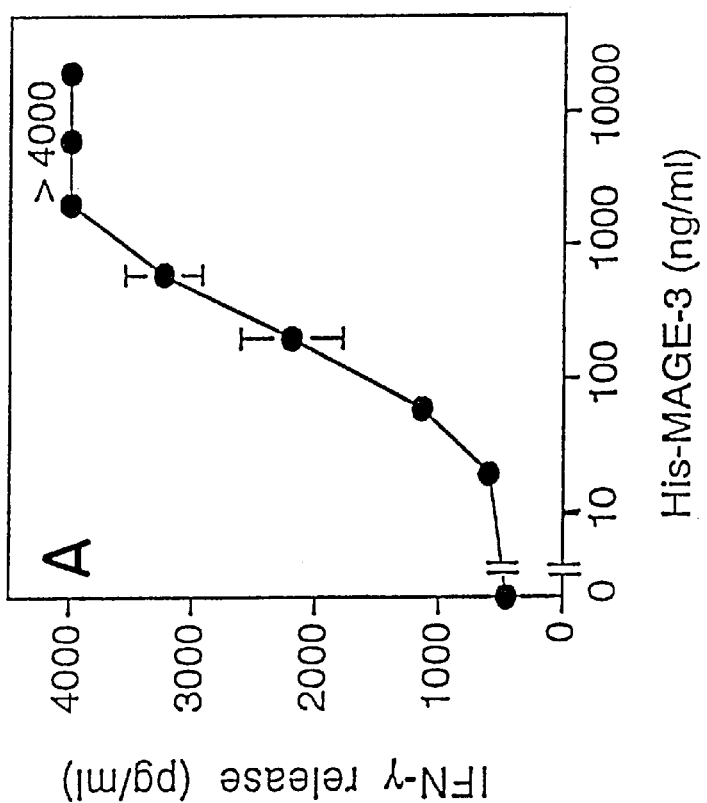
Fig. 9B
Fig. 9A

```
                         SEQUENCE LISTING

<160> NUMBER OF SEQ ID NOS: 81

<210> SEQ ID NO 1
<211> LENGTH: 4204
<212> TYPE: DNA
<213> ORGANISM: Homo sapiens
<220> FEATURE:
<221> NAME/KEY: CDS
<222> LOCATION: 2465..3406

<400> SEQUENCE: 1
acgcaggcag tgatgtcacc cagaccacac cccttccccc aatgccactt caggggtac      60 tcagagtcag agacttggtc tgaggggagc agaagcaatc tgcagaggat ggcggtccag    120
gctcagccag gcatcaactt caggaccctg agggatgacc gaaggccccg cccacccacc    180
cccaactccc ccgaccccac caggatctac agcctcagga ccccgtccc aatccttacc     240 ccttgcccca tcaccatctt catgcttacc tccaccccca tccgatcccc atccaggcag    300
aatccagttc caccctgcc cggaacccag ggtagtaccg ttgccaggat gtgacgccac     360
tgacttgcgc attggaggtc agaagaccgc gagattctcg ccctgagcaa cgagcgacgg    420
cctgacgtcg gcggagggaa gccggcccag gctcggtgag gaggcaaggt aagacgctga    480
gggaggactg aggcgggcct cacctcagac agagggcctc aaataatcca gtgctgcctc    540
tgctgccggg cctgggccac cccgcagggg aagacttcca ggctgggtcg ccactacctc    600
accccgccga ccccgccgc tttagccacg gggaactctg gggacagagc ttaatgtggc     660
cagggcaggg ctggttagaa gaggtcaggg cccacgctgt ggcaggaatc aaggtcagga    720
ccccgagagg gaactgaggg cagcctaacc accaccctca ccaccattcc cgtcccccaa    780
cacccaaccc caccccatc ccccattccc atccccaccc ccaccctat cctggcagaa      840 tccgggcttt gccctggta tcaagtcacg gaagctccgg gaatggcggc caggcacgtg     900
agtcctgagg ttcacatcta cggctaaggg agggaagggg ttcggtatcg cgagtatggc    960
cgttgggagg cagcgaaagg gcccaggcct cctggaagac agtggagtcc tgagggacc   1020 cagcatgcca ggacagggg cccactgtac ccctgtctca aaccgaggca ccttttcatt   1080
cggctacggg aatcctaggg atgcagaccc acttcagcag gggttgggg cccagccctg   1140 cgaggagtca tggggaggaa gaagagggag gactgagggg accttggagt ccagatcagt   1200
ggcaaccttg gctgggga tgctgggcac agtggccaaa tgtgctctgt gctcattgcg    1260 ccttcaggt gaccagagag ttgagggctg tggtctgaag agtgggactt caggtcagca   1320
gagggaggaa tcccaggatc tgcagggccc aaggtgtacc cccaagggc ccctatgtgg   1380 tggacagatg cagtggtcct aggatctgcc aagcatccag gtgaagagac tgagggagga   1440
ttgagggtac ccctgggaca gaatgcggac tggggccccc ataaaaatct gccctgctcc   1500
tgctgttacc tcagagagcc tggcagggc tgtcagctga ggtccctcca ttatcctagg   1560
atcactgatg tcagggaagg ggaagccttg gtctgagggg gctgcactca ggcagtaga    1620 gggaggctct cagaccctac taggagtgga ggtgaggacc aagcagtctc ctcacccagg   1680
gtacatggac ttcaataaat ttggcatctc tcgttgtcc tttcgggag gacctgggaa    1740 tgtatggcca gatgtgggtc ccctcatgtt tttctgtacc atatcaggta tgtgagttct   1800
```

```
                                    -continued tgacatgaga gattctcagg ccagcagaag ggagggatta ggccctataa ggagaaaggt    1860
gagggccctg agtgagcaca gaggggatcc tccacccag tagagtgggg acctcacaga    1920
gtctggccaa ccctcctgac agttctggga atccgtggct gcgtttgctg tctgcacatt    1980
gggggcccgt ggattcctct cccaggaatc aggagctcca ggaacaaggc agtgaggact    2040
tggtctgagg cagtgtcctc aggtcacaga gtagaggggg ctcagatagt gccaacggtg    2100
aaggtttgcc ttggattcaa accaagggcc ccacctgccc cagaacacat ggactccaga    2160
gcgcctggcc tcaccctcaa tactttcagt cctgcagcct cagcatgcgc tggccggatg    2220
taccctgagg tgccctctca cttcctcctt caggttctga ggggacaggc tgacctggag    2280
gaccagaggc ccccggagga gcactgaagg agaagatctg taagtaagcc tttgttagag    2340
cctccaaggt tccattcagt actcagctga ggtctctcac atgctccctc tctccccagg    2400
ccagtgggtc tccattgccc agctcctgcc cacactcccg cctgttgccc tgaccagagt    2460
```

| | | |
|---|---|---|
| catc atg cct ctt gag cag agg agt cag cac tgc aag cct gaa gaa ggc | 2509 | |
|     Met Pro Leu Glu Gln Arg Ser Gln His Cys Lys Pro Glu Glu Gly | | |
|      1             5            10         15 | | |

```
ctt gag gcc cga gga gag gcc ctg ggc ctg gtg ggt gcg cag gct cct    2557
Leu Glu Ala Arg Gly Glu Ala Leu Gly Leu Val Gly Ala Gln Ala Pro
            20                  25                  30 gct act gag gag cag gag gct gcc tcc tcc tct tct act cta gtt gaa    2605
Ala Thr Glu Glu Gln Glu Ala Ala Ser Ser Ser Ser Thr Leu Val Glu
        35                  40                  45 gtc acc ctg ggg gag gtg cct gct gcc gag tca cca gat cct ccc cag    2653
Val Thr Leu Gly Glu Val Pro Ala Ala Glu Ser Pro Asp Pro Pro Gln
    50                  55                  60 agt cct cag gga gcc tcc agc ctc ccc act acc atg aac tac cct ctc    2701
Ser Pro Gln Gly Ala Ser Ser Leu Pro Thr Thr Met Asn Tyr Pro Leu
65                  70                  75 tgg agc caa tcc tat gag gac tcc agc aac caa gaa gag gag ggg cca    2749
Trp Ser Gln Ser Tyr Glu Asp Ser Ser Asn Gln Glu Glu Glu Gly Pro
80                  85                  90                  95 agc acc ttc cct gac ctg gag tcc gag ttc caa gca gca ctc agt agg    2797
Ser Thr Phe Pro Asp Leu Glu Ser Glu Phe Gln Ala Ala Leu Ser Arg
                100                 105                 110 aag gtg gcc gag ttg gtt cat ttt ctg ctc ctc aag tat cga gcc agg    2845
Lys Val Ala Glu Leu Val His Phe Leu Leu Leu Lys Tyr Arg Ala Arg
            115                 120                 125 gag ccg gtc aca aag gca gaa atg ctg ggg agt gtc gtc gga aat tgg    2893
Glu Pro Val Thr Lys Ala Glu Met Leu Gly Ser Val Val Gly Asn Trp
        130                 135                 140 cag tat ttc ttt cct gtg atc ttc agc aaa gct tcc agt tcc ttg cag    2941
Gln Tyr Phe Phe Pro Val Ile Phe Ser Lys Ala Ser Ser Ser Leu Gln
    145                 150                 155 ctg gtc ttt ggc atc gag ctg atg gaa gtg gac ccc atc ggc cac ttg    2989
Leu Val Phe Gly Ile Glu Leu Met Glu Val Asp Pro Ile Gly His Leu
160                 165                 170                 175 tac atc ttt gcc acc tgc ctg ggc ctc tcc tac gat ggc ctg ctg ggt    3037
Tyr Ile Phe Ala Thr Cys Leu Gly Leu Ser Tyr Asp Gly Leu Leu Gly
                180                 185                 190 gac aat cag atc atg ccc aag gca ggc ctc ctg ata atc gtc ctg gcc    3085
Asp Asn Gln Ile Met Pro Lys Ala Gly Leu Leu Ile Ile Val Leu Ala
            195                 200                 205 ata atc gca aga gag ggc gac tgt gcc cct gag gag aaa atc tgg gag    3133
Ile Ile Ala Arg Glu Gly Asp Cys Ala Pro Glu Glu Lys Ile Trp Glu
        210                 215                 220 gag ctg agt gtg tta gag gtg ttt gag ggg agg gaa gac agt atc ttg    3181
```

```
Glu Leu Ser Val Leu Glu Val Phe Gly Arg Glu Asp Ser Ile Leu
    225                 230                 235 ggg gat ccc aag aag ctg ctc acc caa cat ttc gtg cag gaa aac tac    3229
Gly Asp Pro Lys Lys Leu Leu Thr Gln His Phe Val Gln Glu Asn Tyr
240                 245                 250                 255 ctg gag tac cgg cag gtc ccc ggc agt gat cct gca tgt tat gaa ttc    3277
Leu Glu Tyr Arg Gln Val Pro Gly Ser Asp Pro Ala Cys Tyr Glu Phe
                260                 265                 270 ctg tgg ggt cca agg gcc ctc gtt gaa acc agc tat gtg aaa gtc ctg    3325
Leu Trp Gly Pro Arg Ala Leu Val Glu Thr Ser Tyr Val Lys Val Leu
            275                 280                 285 cac cat atg gta aag atc agt gga gga cct cac att tcc tac cca ccc    3373
His His Met Val Lys Ile Ser Gly Gly Pro His Ile Ser Tyr Pro Pro
        290                 295                 300 ctg cat gag tgg gtt ttg aga gag ggg gaa gag tgagtctgag cacgagttgc    3426
Leu His Glu Trp Val Leu Arg Glu Gly Glu Glu
    305                 310 agccagggcc agtgggaggg ggtctgggcc agtgcacctt ccgggccgc atcccttagt      3486
ttccactgcc tcctgtgacg tgaggcccat tcttcactct tgaagcgag cagtcagcat      3546
tcttagtagt gggtttctgt tctgttggat gactttgaga ttattctttg tttcctgttg    3606
gagttgttca aatgttcctt ttaacggatg gttgaatgag cgtcagcatc caggtttatg    3666
aatgacagta gtcacacata gtgctgttta tatagtttag gagtaagagt cttgtttttt    3726
actcaaattg ggaaatccat tccattttgt gaattgtgac ataataatag cagtggtaaa    3786
agtatttgct taaaattgtg agcgaattag caataacata catgagataa ctcaagaaat    3846
caaaagatag ttgattcttg ccttgtacct caatctattc tgtaaaatta aacaaatatg    3906
caaaccagga tttccttgac ttctttgaga atgcaagcga aattaaatct gaataaataa    3966
ttcttcctct tcactggctc gtttcttttc cgttcactca gcatctgctc tgtgggaggc    4026
cctgggttag tagtggggat gctaaggtaa gccagactca cgcctaccca tagggctgta    4086
gagcctagga cctgcagtca tataattaag gtggtgagaa gtcctgtaag atgtagagga    4146
aatgtaagag agggtgagg gtgtggcgct ccgggtgaga gtagtggagt gtcagtgc       4204

<210> SEQ ID NO 2
<211> LENGTH: 314
<212> TYPE: PRT
<213> ORGANISM: Homo sapiens

<400> SEQUENCE: 2

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Gly Pro Ser
                85                  90                  95

Thr Phe Pro Asp Leu Glu Ser Glu Phe Gln Ala Ala Leu Ser Arg Lys
                100                 105                 110

Val Ala Glu Leu Val His Phe Leu Leu Leu Lys Tyr Arg Ala Arg Glu
```

```
                115                 120                   125
Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
                180                 185                 190

Asn Gln Ile Met Pro Lys Ala Gly Leu Leu Ile Ile Val Leu Ala Ile
                195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
                260                 265                 270

Trp Gly Pro Arg Ala Leu Val Glu Thr Ser Tyr Val Lys Val Leu His
                275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

<210> SEQ ID NO 3
<211> LENGTH: 16
<212> TYPE: PRT
<213> ORGANISM: Homo sapiens

<400> SEQUENCE: 3

Arg Lys Val Ala Glu Leu Val His Phe Leu Leu Leu Lys Tyr Arg Ala
1               5                   10                  15

<210> SEQ ID NO 4
<211> LENGTH: 16
<212> TYPE: PRT
<213> ORGANISM: Homo sapiens

<400> SEQUENCE: 4

Glu Leu Val His Phe Leu Leu Leu Lys Tyr Arg Ala Arg Glu Pro Val
1               5                   10                  15

<210> SEQ ID NO 5
<211> LENGTH: 16
<212> TYPE: PRT
<213> ORGANISM: Homo sapiens

<400> SEQUENCE: 5

Arg Glu Pro Val Thr Lys Ala Glu Met Leu Gly Ser Val Val Gly Asn
1               5                   10                  15

<210> SEQ ID NO 6
<211> LENGTH: 16
<212> TYPE: PRT
<213> ORGANISM: Homo sapiens

<400> SEQUENCE: 6
```

Gln Leu Val Phe Gly Ile Glu Leu Met Glu Val Asp Pro Ile Gly His
1               5                   10                  15

<210> SEQ ID NO 7
<211> LENGTH: 8
<212> TYPE: PRT
<213> ORGANISM: Homo sapiens

<400> SEQUENCE: 7

Leu Val His Phe Leu Leu Leu Lys
1               5

<210> SEQ ID NO 8
<211> LENGTH: 9
<212> TYPE: PRT
<213> ORGANISM: Homo sapiens

<400> SEQUENCE: 8

Glu Leu Val His Phe Leu Leu Leu Lys
1               5

<210> SEQ ID NO 9
<211> LENGTH: 12
<212> TYPE: PRT
<213> ORGANISM: Homo sapiens

<400> SEQUENCE: 9

Glu Leu Val His Phe Leu Leu Leu Lys Tyr Arg Ala
1               5                   10

<210> SEQ ID NO 10
<211> LENGTH: 11
<212> TYPE: PRT
<213> ORGANISM: Homo sapiens

<400> SEQUENCE: 10

Leu Val His Phe Leu Leu Leu Lys Tyr Arg Ala
1               5                   10

<210> SEQ ID NO 11
<211> LENGTH: 10
<212> TYPE: PRT
<213> ORGANISM: Homo sapiens

<400> SEQUENCE: 11

Val His Phe Leu Leu Leu Lys Tyr Arg Ala
1               5                   10

<210> SEQ ID NO 12
<211> LENGTH: 9
<212> TYPE: PRT
<213> ORGANISM: Homo sapiens

<400> SEQUENCE: 12

His Phe Leu Leu Leu Lys Tyr Arg Ala
1               5

<210> SEQ ID NO 13
<211> LENGTH: 30
<212> TYPE: DNA
<213> ORGANISM: Homo sapiens

<400> SEQUENCE: 13
gttcattttc tgctcctcaa gtatcgagcc                              30

<210> SEQ ID NO 14
<211> LENGTH: 30
<212> TYPE: DNA
<213> ORGANISM: Homo sapiens

<400> SEQUENCE: 14
tttccatggc tcttgagcag aggagtcagc                                    30

<210> SEQ ID NO 15
<211> LENGTH: 28
<212> TYPE: DNA
<213> ORGANISM: Homo sapiens

<400> SEQUENCE: 15
cccagatctt cactcttccc cctctctc                                      28

<210> SEQ ID NO 16
<211> LENGTH: 23
<212> TYPE: DNA
<213> ORGANISM: Homo sapiens

<400> SEQUENCE: 16
tttccatgga tgaccagcgc gac                                           23

<210> SEQ ID NO 17
<211> LENGTH: 30
<212> TYPE: DNA
<213> ORGANISM: Homo sapiens

<400> SEQUENCE: 17
tttggatccg gaagcttcat gcgcaggttc                                    30

<210> SEQ ID NO 18
<211> LENGTH: 26
<212> TYPE: DNA
<213> ORGANISM: Homo sapiens

<400> SEQUENCE: 18
tttagatctt gagcagagga gtcagc                                        26

<210> SEQ ID NO 19
<211> LENGTH: 20
<212> TYPE: DNA
<213> ORGANISM: Homo sapiens

<400> SEQUENCE: 19
cccccatggc ggcccccggc                                               20

<210> SEQ ID NO 20
<211> LENGTH: 23
<212> TYPE: DNA
<213> ORGANISM: Homo sapiens

<400> SEQUENCE: 20
gggggatcct caaagagtgc tga                                           23

<210> SEQ ID NO 21
<211> LENGTH: 28
<212> TYPE: DNA
<213> ORGANISM: Homo sapiens

<400> SEQUENCE: 21
gggggatcct aacaacatgt tgatcccc                                      28

<210> SEQ ID NO 22
<211> LENGTH: 36
<212> TYPE: DNA
<213> ORGANISM: Homo sapiens

<400> SEQUENCE: 22
gggagatctc tagatggtct gggtctgata gccggc            36

<210> SEQ ID NO 23
<211> LENGTH: 16
<212> TYPE: PRT
<213> ORGANISM: Homo sapiens

<400> SEQUENCE: 23

Phe Leu Leu Leu Lys Tyr Arg Ala Arg Glu Pro Val Thr Lys Ala Glu
 1               5                  10                  15

<210> SEQ ID NO 24
<211> LENGTH: 16
<212> TYPE: PRT
<213> ORGANISM: Homo sapiens

<400> SEQUENCE: 24

Val Ala Glu Leu Val His Phe Leu Leu Leu Lys Tyr Arg Ala Arg Glu
 1               5                  10                  15

<210> SEQ ID NO 25
<211> LENGTH: 15
<212> TYPE: PRT
<213> ORGANISM: Homo sapiens

<400> SEQUENCE: 25

Val Ala Glu Leu Val His Phe Leu Leu Leu Lys Tyr Arg Ala Arg
 1               5                  10                  15

<210> SEQ ID NO 26
<211> LENGTH: 14
<212> TYPE: PRT
<213> ORGANISM: Homo sapiens

<400> SEQUENCE: 26

Val Ala Glu Leu Val His Phe Leu Leu Leu Lys Tyr Arg Ala
 1               5                  10

<210> SEQ ID NO 27
<211> LENGTH: 15
<212> TYPE: PRT
<213> ORGANISM: Homo sapiens

<400> SEQUENCE: 27

Ala Glu Leu Val His Phe Leu Leu Leu Lys Tyr Arg Ala Arg Glu
 1               5                  10                  15

<210> SEQ ID NO 28
<211> LENGTH: 14
<212> TYPE: PRT
<213> ORGANISM: Homo sapiens

<400> SEQUENCE: 28

Ala Glu Leu Val His Phe Leu Leu Leu Lys Tyr Arg Ala Arg
 1               5                  10

<210> SEQ ID NO 29

<211> LENGTH: 13
<212> TYPE: PRT
<213> ORGANISM: Homo sapiens

<400> SEQUENCE: 29

```
Ala Glu Leu Val His Phe Leu Leu Leu Lys Tyr Arg Ala
 1               5                  10
```

<210> SEQ ID NO 30
<211> LENGTH: 14
<212> TYPE: PRT
<213> ORGANISM: Homo sapiens

<400> SEQUENCE: 30

```
Glu Leu Val His Phe Leu Leu Leu Lys Tyr Arg Ala Arg Glu
 1               5                  10
```

<210> SEQ ID NO 31
<211> LENGTH: 13
<212> TYPE: PRT
<213> ORGANISM: Homo sapiens

<400> SEQUENCE: 31

```
Glu Leu Val His Phe Leu Leu Leu Lys Tyr Arg Ala Arg
 1               5                  10
```

<210> SEQ ID NO 32
<211> LENGTH: 15
<212> TYPE: PRT
<213> ORGANISM: Homo sapiens

<400> SEQUENCE: 32

```
Phe Leu Leu Leu Lys Tyr Arg Ala Arg Glu Pro Val Thr Lys Ala
 1               5                  10                  15
```

<210> SEQ ID NO 33
<211> LENGTH: 14
<212> TYPE: PRT
<213> ORGANISM: Homo sapiens

<400> SEQUENCE: 33

```
Phe Leu Leu Leu Lys Tyr Arg Ala Arg Glu Pro Val Thr Lys
 1               5                  10
```

<210> SEQ ID NO 34
<211> LENGTH: 13
<212> TYPE: PRT
<213> ORGANISM: Homo sapiens

<400> SEQUENCE: 34

```
Phe Leu Leu Leu Lys Tyr Arg Ala Arg Glu Pro Val Thr
 1               5                  10
```

<210> SEQ ID NO 35
<211> LENGTH: 12
<212> TYPE: PRT
<213> ORGANISM: Homo sapiens

<400> SEQUENCE: 35

```
Phe Leu Leu Leu Lys Tyr Arg Ala Arg Glu Pro Val
 1               5                  10
```

<210> SEQ ID NO 36
<211> LENGTH: 11
<212> TYPE: PRT

<213> ORGANISM: Homo sapiens

<400> SEQUENCE: 36

Phe Leu Leu Leu Lys Tyr Arg Ala Arg Glu Pro
 1               5                  10

<210> SEQ ID NO 37
<211> LENGTH: 15
<212> TYPE: PRT
<213> ORGANISM: Homo sapiens

<400> SEQUENCE: 37

Leu Leu Leu Lys Tyr Arg Ala Arg Glu Pro Val Thr Lys Ala Glu
 1               5                  10                  15

<210> SEQ ID NO 38
<211> LENGTH: 14
<212> TYPE: PRT
<213> ORGANISM: Homo sapiens

<400> SEQUENCE: 38

Leu Leu Lys Tyr Arg Ala Arg Glu Pro Val Thr Lys Ala Glu
 1               5                  10

<210> SEQ ID NO 39
<211> LENGTH: 13
<212> TYPE: PRT
<213> ORGANISM: Homo sapiens

<400> SEQUENCE: 39

Leu Lys Tyr Arg Ala Arg Glu Pro Val Thr Lys Ala Glu
 1               5                  10

<210> SEQ ID NO 40
<211> LENGTH: 12
<212> TYPE: PRT
<213> ORGANISM: Homo sapiens

<400> SEQUENCE: 40

Lys Tyr Arg Ala Arg Glu Pro Val Thr Lys Ala Glu
 1               5                  10

<210> SEQ ID NO 41
<211> LENGTH: 10
<212> TYPE: PRT
<213> ORGANISM: Homo sapiens

<400> SEQUENCE: 41

Leu Val His Phe Leu Leu Leu Lys Tyr Arg
 1               5                  10

<210> SEQ ID NO 42
<211> LENGTH: 10
<212> TYPE: PRT
<213> ORGANISM: Homo sapiens

<400> SEQUENCE: 42

Leu Lys Tyr Arg Ala Arg Glu Pro Val Thr
 1               5                  10

<210> SEQ ID NO 43
<211> LENGTH: 30
<212> TYPE: DNA
<213> ORGANISM: Homo sapiens

```
<400> SEQUENCE: 43 tggttcatt ttctgctcct caagtatcga                                    30

<210> SEQ ID NO 44
<211> LENGTH: 30
<212> TYPE: DNA
<213> ORGANISM: Homo sapiens

<400> SEQUENCE: 44
ctcaagtatc gagccaggga gccggtcaca                                   30

<210> SEQ ID NO 45
<211> LENGTH: 9
<212> TYPE: PRT
<213> ORGANISM: Homo sapiens

<400> SEQUENCE: 45

Glu Ala Asp Pro Thr Gly His Ser Tyr
 1               5

<210> SEQ ID NO 46
<211> LENGTH: 9
<212> TYPE: PRT
<213> ORGANISM: Homo sapiens

<400> SEQUENCE: 46

Ser Ala Tyr Gly Glu Pro Arg Lys Leu
 1               5

<210> SEQ ID NO 47
<211> LENGTH: 9
<212> TYPE: PRT
<213> ORGANISM: Homo sapiens

<400> SEQUENCE: 47

Glu Val Asp Pro Ile Gly His Leu Tyr
 1               5

<210> SEQ ID NO 48
<211> LENGTH: 9
<212> TYPE: PRT
<213> ORGANISM: Homo sapiens

<400> SEQUENCE: 48

Phe Leu Trp Gly Pro Arg Ala Leu Val
 1               5

<210> SEQ ID NO 49
<211> LENGTH: 10
<212> TYPE: PRT
<213> ORGANISM: Homo sapiens

<400> SEQUENCE: 49

Met Glu Val Asp Pro Ile Gly His Leu Tyr
 1               5                  10

<210> SEQ ID NO 50
<211> LENGTH: 9
<212> TYPE: PRT
<213> ORGANISM: Homo sapiens

<400> SEQUENCE: 50

Ala Ala Arg Ala Val Phe Leu Ala Leu
 1               5
```

<210> SEQ ID NO 51
<211> LENGTH: 8
<212> TYPE: PRT
<213> ORGANISM: Homo sapiens

<400> SEQUENCE: 51

Tyr Arg Pro Arg Pro Arg Arg Tyr
 1               5

<210> SEQ ID NO 52
<211> LENGTH: 10
<212> TYPE: PRT
<213> ORGANISM: Homo sapiens

<400> SEQUENCE: 52

Ser Pro Ser Ser Asn Arg Ile Arg Asn Thr
 1               5                  10

<210> SEQ ID NO 53
<211> LENGTH: 9
<212> TYPE: PRT
<213> ORGANISM: Homo sapiens

<400> SEQUENCE: 53

Val Leu Pro Asp Val Phe Ile Arg Cys
 1               5

<210> SEQ ID NO 54
<211> LENGTH: 10
<212> TYPE: PRT
<213> ORGANISM: Homo sapiens

<400> SEQUENCE: 54

Val Leu Pro Asp Val Phe Ile Arg Cys Val
 1               5                  10

<210> SEQ ID NO 55
<211> LENGTH: 9
<212> TYPE: PRT
<213> ORGANISM: Homo sapiens

<400> SEQUENCE: 55

Glu Glu Lys Leu Ile Val Val Leu Phe
 1               5

<210> SEQ ID NO 56
<211> LENGTH: 9
<212> TYPE: PRT
<213> ORGANISM: Homo sapiens

<400> SEQUENCE: 56

Glu Glu Lys Leu Ser Val Val Leu Phe
 1               5

<210> SEQ ID NO 57
<211> LENGTH: 10
<212> TYPE: PRT
<213> ORGANISM: Homo sapiens

<400> SEQUENCE: 57

Ala Cys Asp Pro His Ser Gly His Phe Val
 1               5                  10

<210> SEQ ID NO 58
<211> LENGTH: 10
<212> TYPE: PRT
<213> ORGANISM: Homo sapiens

<400> SEQUENCE: 58

Ala Arg Asp Pro His Ser Gly His Phe Val
 1               5                  10

<210> SEQ ID NO 59
<211> LENGTH: 9
<212> TYPE: PRT
<213> ORGANISM: Homo sapiens

<400> SEQUENCE: 59

Ser Tyr Leu Asp Ser Gly Ile His Phe
 1               5

<210> SEQ ID NO 60
<211> LENGTH: 9
<212> TYPE: PRT
<213> ORGANISM: Homo sapiens

<400> SEQUENCE: 60

Ser Tyr Leu Asp Ser Gly Ile His Ser
 1               5

<210> SEQ ID NO 61
<211> LENGTH: 9
<212> TYPE: PRT
<213> ORGANISM: Homo sapiens

<400> SEQUENCE: 61

Met Leu Leu Ala Val Leu Tyr Cys Leu
 1               5

<210> SEQ ID NO 62
<211> LENGTH: 9
<212> TYPE: PRT
<213> ORGANISM: Homo sapiens

<400> SEQUENCE: 62

Tyr Met Asn Gly Thr Met Ser Gln Val
 1               5

<210> SEQ ID NO 63
<211> LENGTH: 9
<212> TYPE: PRT
<213> ORGANISM: Homo sapiens

<400> SEQUENCE: 63

Ala Phe Leu Pro Trp His Arg Leu Phe
 1               5

<210> SEQ ID NO 64
<211> LENGTH: 9
<212> TYPE: PRT
<213> ORGANISM: Homo sapiens

<400> SEQUENCE: 64

Ser Glu Ile Trp Arg Asp Ile Asp Phe
 1               5

<210> SEQ ID NO 65
<211> LENGTH: 9

```
<212> TYPE: PRT
<213> ORGANISM: Homo sapiens

<400> SEQUENCE: 65

Tyr Glu Ile Trp Arg Asp Ile Asp Phe
 1               5

<210> SEQ ID NO 66
<211> LENGTH: 15
<212> TYPE: PRT
<213> ORGANISM: Homo sapiens

<400> SEQUENCE: 66

Gln Asn Ile Leu Leu Ser Asn Ala Pro Leu Gly Pro Gln Phe Pro
 1               5                  10                  15

<210> SEQ ID NO 67
<211> LENGTH: 15
<212> TYPE: PRT
<213> ORGANISM: Homo sapiens

<400> SEQUENCE: 67

Asp Tyr Ser Tyr Leu Gln Asp Ser Asp Pro Asp Ser Phe Gln Asp
 1               5                  10                  15

<210> SEQ ID NO 68
<211> LENGTH: 10
<212> TYPE: PRT
<213> ORGANISM: Homo sapiens

<400> SEQUENCE: 68

Glu Ala Ala Gly Ile Gly Ile Leu Thr Val
 1               5                  10

<210> SEQ ID NO 69
<211> LENGTH: 9
<212> TYPE: PRT
<213> ORGANISM: Homo sapiens

<400> SEQUENCE: 69

Ala Ala Gly Ile Gly Ile Leu Thr Val
 1               5

<210> SEQ ID NO 70
<211> LENGTH: 9
<212> TYPE: PRT
<213> ORGANISM: Homo sapiens

<400> SEQUENCE: 70

Ile Leu Thr Val Ile Leu Gly Val Leu
 1               5

<210> SEQ ID NO 71
<211> LENGTH: 9
<212> TYPE: PRT
<213> ORGANISM: Homo sapiens

<400> SEQUENCE: 71

Lys Thr Trp Gly Gln Tyr Trp Gln Val
 1               5

<210> SEQ ID NO 72
<211> LENGTH: 9
<212> TYPE: PRT
<213> ORGANISM: Homo sapiens
```

```
<400> SEQUENCE: 72

Ile Thr Asp Gln Val Pro Phe Ser Val
 1               5

<210> SEQ ID NO 73
<211> LENGTH: 9
<212> TYPE: PRT
<213> ORGANISM: Homo sapiens

<400> SEQUENCE: 73

Tyr Leu Glu Pro Gly Pro Val Thr Ala
 1               5

<210> SEQ ID NO 74
<211> LENGTH: 10
<212> TYPE: PRT
<213> ORGANISM: Homo sapiens

<400> SEQUENCE: 74

Leu Leu Asp Gly Thr Ala Thr Leu Arg Leu
 1               5                  10

<210> SEQ ID NO 75
<211> LENGTH: 10
<212> TYPE: PRT
<213> ORGANISM: Homo sapiens

<400> SEQUENCE: 75

Val Leu Tyr Arg Tyr Gly Ser Phe Ser Val
 1               5                  10

<210> SEQ ID NO 76
<211> LENGTH: 9
<212> TYPE: PRT
<213> ORGANISM: Homo sapiens

<400> SEQUENCE: 76

Leu Tyr Val Asp Ser Leu Phe Phe Leu
 1               5

<210> SEQ ID NO 77
<211> LENGTH: 12
<212> TYPE: PRT
<213> ORGANISM: Homo sapiens

<400> SEQUENCE: 77

Lys Ile Ser Gly Gly Pro Arg Ile Ser Tyr Pro Leu
 1               5                  10

<210> SEQ ID NO 78
<211> LENGTH: 9
<212> TYPE: PRT
<213> ORGANISM: Homo sapiens

<400> SEQUENCE: 78

Tyr Met Asp Gly Thr Met Ser Gln Val
 1               5

<210> SEQ ID NO 79
<211> LENGTH: 11
<212> TYPE: PRT
<213> ORGANISM: Homo sapiens

<400> SEQUENCE: 79
```

-continued

```
Ser Leu Leu Met Trp Ile Thr Gln Cys Phe Leu
  1               5                  10

<210> SEQ ID NO 80
<211> LENGTH: 9
<212> TYPE: PRT
<213> ORGANISM: Homo sapiens

<400> SEQUENCE: 80

Ser Leu Leu Met Trp Ile Thr Gln Cys
  1               5

<210> SEQ ID NO 81
<211> LENGTH: 9
<212> TYPE: PRT
<213> ORGANISM: Homo sapiens

<400> SEQUENCE: 81

Gln Leu Ser Leu Leu Met Trp Ile Thr
  1               5
```

MAGE-3 PEPTIDES PRESENTED BY HLA CLASS II MOLECULES

RELATED APPLICATIONS

This application is a continuation of U.S. patent application Ser. No. 09/166,448, filed on Oct. 5, 1998, now U.S. Pat. No. 6,291,430, which is a continuation-in-part of U.S. patent application Ser. No. 08/928,615, filed on Sep. 12, 1997, now U.S. Pat. No. 5,965,535 the disclosure of which is incorporated herein by reference.

FIELD OF THE INVENTION

This invention relates to fragments of the tumor associated gene product MAGE-3 which bind to and are presented to T lymphocytes by HLA class II molecules. The peptides, nucleic acid molecules which code for such peptides, as well as related antibodies and CD4$^+$ T lymphocytes, are useful, inter alia, in diagnostic and therapeutic contexts.

BACKGROUND OF THE INVENTION

The process by which the mammalian immune system recognizes and reacts to foreign or alien materials is complex. An important facet of the system is the T cell response, which in part comprises mature T lymphocytes which are positive for either CD4 or CD8 cell surface proteins. T cells can recognize and interact with other cells via cell surface complexes on the other cells of peptides and molecules referred to as human leukocyte antigens ("HLAs") or major histocompatibility complexes ("MHCs"). The peptides are derived from larger molecules which are processed by the cells which also present the HLA/MHC molecule. See Male et al., *Advanced Immunology* (J. P. Lipincott Company, 1987), especially chapters 6–10. The interaction of T cells and complexes of HLA/peptide is restricted, requiring a specific T cell for a specific complex of an HLA molecule and a peptide. If a specific T cell is not present, there is no T cell response even if its partner complex is present. Similarly, there is no response if the specific complex is absent, but the T cell is present. The mechanisms described above are involved in the immune system's response to foreign materials, in autoimmune pathologies, and in responses to cellular abnormalities.

The T cell response to foreign antigens includes both cytolytic T lymphocytes and helper T lymphocytes. CD8$^+$ cytotoxic or cytolytic T cells (CTLS) are T cells which, when activated, lyse cells that present the appropriate antigen presented by HLA class I molecules. CD4$^+$ T helper cells are T cells which secrete cytokines to stimulate macrophages and antigen-producing B cells which present the appropriate antigen by HLA class II molecules on their surface.

The mechanism by which T cells recognize alien materials also has been implicated in cancer. A number of cytolytic T lymphocyte (CTL) clones directed against autologous melanoma have been described. In some instances, the antigens recognized by these clones have been characterized. In De Plaen et al., *Immunogenetics* 40:360–369 (1994), the "MAGE" family, a family of genes encoding tumor specific antigens, is described. (See also PCT application PCT/US92/04354, published on Nov. 26, 1992.) The expression products of these genes are processed into peptides which, in turn, are expressed on cell surfaces. This can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *Immunogenetics* 35: 145 (1992); van der Bruggen et al., *Science* 254: 1643 (1991), for further information on this family of genes. Also, see U.S. Pat. No. 5,342,774.

In U.S. Pat. No. 5,405,940, MAGE nonapeptides are taught which are presented by the HLA-A1 molecule. Given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. Pat. No. 5,591,430, additional isolated MAGE-3 peptides are taught which are presented by the HLA-A2 molecule. Therefore, a given TRAP can yield a plurality of TRAs.

The foregoing references describe isolation and/or characterization of tumor rejection antigens which are presented by HLA class I molecules. These TRAs can induce activation and proliferation of CD8$^+$ cytotoxic T lymphocytes (CTLs) which recognize tumor cells that express the tumor associated genes (e.g. MAGE genes) which encode the TRAs.

The importance of CD4$^+$ T lymphocytes (helper T cells) in antitumor immunity has been demonstrated in animal models in which these cells not only serve cooperative and effector functions, but are also critical in maintaining immune memory (reviewed by Topalian, *Curr. Opin. Immunol.* 6:741–745, 1994). Moreover, several studies support the contention that poor tumor-specific immunity is due to inadequate activation of T helper cells.

It has recently been demonstrated that the tyrosinase gene encodes peptides which are presented by HLA class II molecules to stimulate CD4$^+$ T lymphocytes; (Topalian et al., 1994; Yee et al., *J. Immunol.* 157:4079–4086, 1996; Topalian et al., *J. Exp. Med.* 183:1965–1971, 1996).

As with many cancer associated antigens, tyrosinase is expressed in a limited percentage of tumors and in limited types of tumors. Furthermore, the two identified MHC class II binding tyrosinase peptides are HLA-DRB 1*0401-restricted peptides, recognized only by cells which express the particular HLA molecule.

Therefore, there exist many patients who would not benefit from any therapy which includes helper T cell stimulation via tyrosinase peptides, either because the patient's tumor does not express tyrosinase, or because the patient does not express the appropriate HLA molecule. Accordingly, there is a need for the identification of additional tumor associated antigens which contain epitopes presented by MHC class II molecules and recognized by CD4$^+$ lymphocytes.

SUMMARY OF THE INVENTION

It now has been discovered that the MAGE-3 gene encodes additional tumor rejection antigens which are HLA class II binding peptides. These peptides, when presented by an antigen presenting cell having an HLA class II molecule, effectively induce the activation and proliferation of CD4$^+$ T lymphocytes.

The invention provides isolated MAGE-3 peptides which bind HLA class II molecules, and functional variants of such peptides, the functional variants comprising one or more amino acid additions, substitutions or deletions to the MAGE-3 peptide sequence. The invention also provides isolated nucleic acid molecules encoding such peptides, expression vectors containing those nucleic acid molecules, host cells transfected with those nucleic acid molecules, and antibodies to those peptides and complexes of the peptides and HLA class II antigen presenting molecules. T lymphocytes which recognize complexes of the peptides and HLA class II antigen presenting molecules are also provided. Kits and vaccine compositions containing the foregoing molecules additionally are provided. The foregoing can be used in the diagnosis or treatment of conditions characterized by the expression of MAGE-3. As it is known that the members of the MAGE family of polypeptides and nucleic acids share significant sequence identity and functional homology (e.g., as tumor antigens and precursors), the invention also embraces HLA binding peptides derived from members of the MAGE family other than MAGE-3. Therefore, it is understood that the disclosure contained herein of MAGE-3 HLA class II binding peptides, compositions containing such peptides, and methods of identifying and using such peptides applies also to other members of the MAGE tumor associated antigen family.

According to one aspect of the invention, an isolated MAGE-3 HLA class II-binding peptide, comprising a fragment of the amino acid sequence of SEQ ID NO:2 which binds an HLA class II molecule, or a functional variant thereof comprising one or more amino acid additions, substitutions or deletions, is provided. The isolated peptide in one embodiment comprises the amino acid sequence of SEQ ID NO:11 or SEQ ID NO:41, or a functional variant thereof. In another embodiment the isolated peptide comprises the amino acid sequence of SEQ ID NO:42, or a functional variant thereof. In certain embodiments, the isolated HLA class II-binding peptide comprises an amino acid sequence selected from the group consisting of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30 and SEQ ID NO:31. In other embodiments, the isolated peptide comprises an amino acid sequence selected from the group consisting of SEQ ID NO:23, SEQ ID NO:32, SEQ ID NO:34, SEQ ID NO:35, SEQ ID NO:37, SEQ ID NO:38 and SEQ ID NO:39. In preferred embodiments, the isolated peptide consists of one of the foregoing amino acid sequences. More preferably, the isolated peptide consists of an amino acid sequence selected from SEQ ID NO:3, SEQ ID NO:4, SEQ ID NO:23, SEQ ID NO:34, SEQ ID NO:37 and SEQ ID NO:38. In certain embodiments, the isolated peptide comprises an endosomal targeting signal, preferably an endosomal targeting portion of human invariant chain Ii. In other embodiments of the invention, the isolated HLA class II-binding peptide is non-hydrolyzable. Preferred non-hydrolyzable peptides are selected from the group consisting of peptides comprising D-amino acids, peptides comprising a -psi[CH$_2$NH]-reduced amide peptide bond, peptides comprising a -psi[COCH$_2$]-ketomethylene peptide bond, peptides comprising a -psi[CH(CN)NH]-(cyanomethylene) amino peptide bond, peptides comprising a -psi[CH$_2$CH(OH)]-hydroxyethylene peptide bond, peptides comprising a -psi[CH$_2$O]-peptide bond, and peptides comprising a -psi[CH$_2$S]-thiomethylene peptide bond.

According to another aspect of the invention, a composition comprising an isolated MAGE-3 HLA class I-binding peptide and an isolated MAGE-3 HLA class II-binding peptide is provided. In certain embodiments, the MAGE-3 HLA class I-binding peptide and the MAGE-3 HLA class II-binding peptide are combined as a polytope polypeptide. In other embodiments the isolated MAGE-3 HLA class II-binding peptide in the composition comprises the amino acid sequence of SEQ ID NO:11, SEQ ID NO:41 SEQ ID NO:42 or a functional variant thereof. Preferably, the isolated MAGE-3 HLA class II-binding peptide in the composition consists of an amino acid sequence selected from the group consisting of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. MAGE-3 HLA class II-binding peptide consists of an amino acid sequence selected from the group consisting of SEQ ID NO:3, SEQ ID NO:4, SEQ ID NO:23, SEQ ID NO:34, SEQ ID NO:37 and SEQ ID NO:38. In certain embodiments of the foregoing compositions, the isolated MAGE-3 HLA class II-binding peptide includes an endosomal targeting signal. Preferably the endosomal targeting signal includes an endosomal targeting portion of human invariant chain Ii.

According to another aspect of the invention, an isolated nucleic acid encoding any of the foregoing HLA class II-binding peptides is provided. Preferably the nucleic acid comprises SEQ ID NO:13, SEQ ID NO:43 or SEQ ID NO:44.

According to still another aspect of the invention, expression vectors are provided. The expression vectors comprise any of the foregoing isolated nucleic acids operably linked to a promoter. In preferred embodiments, the nucleic acid comprises SEQ ID NO:13, SEQ ID NO:43 or SEQ ID NO:44. In other embodiments, the expression vector further comprise a nucleic acid which encodes an HLA-DRB1/13 molecule.

According to yet another aspect of the invention, host cells transfected or transformed with any of the foregoing expression vectors are provided. Host cells which express an HLA-DRB1/13 molecule, and which are transfected or transformed with any of the foregoing expression vectors are also provided.

According to another aspect of the invention, methods for enriching selectively a population of T lymphocytes with CD4$^+$ T lymphocytes specific for a MAGE-3 HLA class II-binding peptide are provided. The methods include contacting an isolated population of T lymphocytes with an agent presenting a complex of the MAGE-3 HLA class II-binding peptide and an HLA class II molecule in an amount sufficient to selectively enrich the isolated population of T lymphocytes with the CD4$^+$T lymphocytes. In certain embodiments, the agent is an antigen presenting cell contacted with a MAGE-3 protein or an HLA class II binding fragment thereof. In preferred embodiments, the HLA class II molecule is an HLA-DRB1/13 molecule and the MAGE-3 HLA class II-binding peptide is a peptide having the amino acid sequence of any of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID NO:3, SEQ ID NO:4, SEQ ID NO:23, SEQ ID NO:34, SEQ ID NO:37 or SEQ ID NO:38. In certain embodiments of the foregoing methods, the isolated MAGE-3 protein or HLA class II binding peptide thereof includes an endosomal targeting signal. Preferably the endosomal targeting signal includes an endosomal targeting portion of human invariant chain Ii.

According to a further aspect of the invention, methods for diagnosing a disorder characterized by expression of MAGE-3 are provided. The methods include contacting a biological sample isolated from a subject with an agent that is specific for the MAGE-3 HLA class II binding peptide, and determining the interaction between the agent and the MAGE-3 HLA class II binding peptide as a determination of the disorder. The biological sample in some embodiments is, for example, dendritic cells loaded with a tumor cell lysate. In certain embodiments, the peptide comprises the amino acid sequence of SEQ ID NO:11, SEQ ID NO:41, SEQ ID NO:42, or a functional variant thereof. In preferred embodiments, the MAGE-3 HLA class II-binding peptide is a peptide having the amino acid sequence of any of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID NO:3, SEQ ID NO:4, SEQ ID NO:23, SEQ ID NO:34, SEQ ID NO:37 or SEQ ID NO:38.

According to another aspect of the invention, methods for diagnosing a disorder characterized by expression of a MAGE-3 HLA class II-binding peptide which forms a complex with an HLA class II molecule are provided. The methods include contacting a biological sample isolated from a subject with an agent that binds the complex; and determining binding between the complex and the agent as a determination of the disorder. In some embodiments the HLA class II molecule is an HLA-DRB1/13 molecule, such as HLA-DRB1/1301 or HLA-DRB1/1302, and the MAGE-3 HLA class II-binding peptide comprises the amino acid sequence of SEQ ID NO:11, SEQ ID NO:41, SEQ ID NO:42, or a functional variant thereof. Preferably the MAGE-3 HLA class II-binding peptide is a peptide having the amino acid sequence of any of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID NO:3, SEQ ID NO:4, SEQ ID NO:23, SEQ ID NO:34, SEQ ID NO:37 or SEQ ID NO:38.

Methods for treating a subject having a disorder characterized by expression of MAGE-3 are provided in another aspect of the invention. The methods include administering to the subject an amount of a MAGE-3 HLA class II-binding peptide sufficient to ameliorate the disorder. In certain embodiments the MAGE-3 HLA class II-binding peptide comprises the amino acid sequence of SEQ ID NO:11, SEQ ID NO:41, SEQ ID NO:42, or a functional variant thereof. Preferably the MAGE-3 HLA class II-binding peptide is a peptide having the amino acid sequence of any of SEQ ID NO:3,SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID NO:3, SEQ ID NO:4, SEQ ID NO:23, SEQ ID NO:34, SEQ ID NO:37 or SEQ ID NO:38. In certain embodiments, the MAGE-3 HLA class II binding peptide comprises an endosomal targeting signal, preferably an endosomal targeting portion of human invariant chain Ii.

According to still another aspect of the invention, methods for treating a subject having a disorder characterized by expression of MAGE-3 are provided. The methods include administering to the subject an amount of a MAGE-3 HLA class I-binding peptide and an amount of a MAGE-3 HLA class II-binding peptide sufficient to ameliorate the disorder. In certain embodiments, the MAGE-3 HLA class II-binding peptide comprises the amino acid sequence of SEQ ID NO:11, SEQ ID NO:41, SEQ ID NO:42, or a functional variant thereof. Preferably the MAGE-3 HLA class II-binding peptide is a peptide having the amino acid sequence of any of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID NO:3, SEQ ID NO:4, SEQ ID NO:23, SEQ ID NO:34, SEQ ID NO:37 or SEQ ID NO:38. In certain embodiment of the foregoing methods, the MAGE-3 HLA class I-binding peptide and the MAGE-3 HLA class II-binding peptide are combined as a polytope polypeptide. In still other embodiments, the MAGE-3 HLA class II binding peptide comprises an endosomal targeting signal, preferably an endosomal targeting portion of human invariant chain Ii.

According to yet another aspect of the invention, methods for treating a subject having a disorder characterized by expression of MAGE-3 are provided. The methods include administering to the subject an amount of an agent which enriches selectively in the subject the presence of complexes of an HLA class II molecule and a MAGE-3 HLA class II-binding peptide, sufficient to ameliorate the disorder. Preferably the HLA class II molecule is an HLA-DRB1/13 molecule, such as HLA-DRB1/1301 or HLA-DRB1/1302. In certain embodiments, the MAGE-3 HLA class II-binding peptide comprises the amino acid sequence of SEQ ID NO:11, SEQ ID NO:41, SEQ ID NO:42, or a functional variant thereof. Preferably the MAGE-3 HLA class II-binding peptide is a peptide having the amino acid sequence of any of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID NO:3, SEQ ID NO:4, SEQ ID NO:23, SEQ ID NO:34, SEQ ID NO:37 or SEQ ID NO:38. In certain embodiments, the agent comprises a MAGE-3 HLA class II binding peptide. Preferably the MAGE-3 HLA class II binding peptide includes an endosomal targeting signal. Preferred endosomal targeting signals include endosomal targeting portion of human invariant chain Ii.

Additional methods for treating a subject having a disorder characterized by expression of MAGE-3 are provided in another aspect of the invention. The methods include administering to the subject an amount of autologous CD4$^+$ T lymphocytes sufficient to ameliorate the disorder, wherein the CD4+ T lymphocytes are specific for complexes of an HLA class II molecule and a MAGE-3 HLA class II-binding peptide. Preferably the HLA class II molecule is an HLA-DRB1/13 molecule, such as HLA-DRB1/1301 or HLA-DRB1/1302. In certain embodiments, the MAGE-3 HLA class II-binding peptide comprises the amino acid sequence of SEQ ID NO:11, SEQ ID NO:41, SEQ ID NO:42, or a functional variant thereof. Preferably the MAGE-3 HLA class II-binding peptide is a peptide having the amino acid sequence of any of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID NO:3, SEQ ID NO:4, SEQ ID NO:23, SEQ ID NO:34, SEQ ID NO:37 or SEQ ID NO:38.

According to another aspect of the invention, an isolated polypeptide is provided. The isolated polypeptide binds selectively a MAGE-3 HLA class II-binding peptide, provided that the isolated polypeptide is not an HLA class II molecule. In certain embodiments, the isolated polypeptide is an antibody and preferably is a monoclonal antibody. In other embodiments, the isolated polypeptide is an antibody fragment selected from the group consisting of a Fab fragment, a F(ab)$_2$ fragment or a fragment including a CDR3 region selective for a MAGE-3 HLA class II-binding peptide.

According to still another aspect of the invention, an isolated CD4+ T lymphocyte is provided. The isolated CD4+ T lymphocyte selectively binds a complex of an HLA class II molecule and a MAGE-3 HLA class II-binding peptide. Preferably the HLA class II molecule is an HLA-DRB1/13 molecule. In some embodiments the MAGE-3 HLA class II-binding peptide comprises the amino acid sequence of SEQ ID NO:11, SEQ ID NO:41, SEQ ID NO:42, or a functional variant thereof. Preferably the MAGE-3 HLA class II-binding peptide is a peptide having the amino acid sequence of any of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID NO:3, SEQ ID NO:4, SEQ ID NO:23; SEQ ID NO:34, SEQ ID NO:37 or SEQ ID NO:38.

According to still another aspect of the invention, an isolated antigen presenting cell is provided. The isolated antigen presenting cell comprises a complex of an HLA class II molecule and a MAGE-3 HLA class II-binding peptide. Preferably the HLA class II molecule is an HLA-DRB1/13 molecule. In certain embodiments the MAGE-3 HLA class II-binding peptide comprises the amino acid sequence of SEQ ID NO:11, SEQ ID NO:41, SEQ ID NO:42, or a functional variant thereof. In preferred embodiments the MAGE-3 HLA class II-binding peptide is a peptide having the amino acid sequence of any of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID, SEQ ID NO:4, SEQ ID NO:23, SEQ ID NO:34, SEQ ID NO:37 or SEQ ID NO:38.

Methods for identifying functional variants of a MAGE-3 HLA class II binding peptide are provided according to another aspect of the invention. According to the methods, a MAGE-3 HLA class II binding peptide, an HLA class II binding molecule which binds the MAGE-3 HLA class II binding peptide, and a T cell which is stimulated by the MAGE-3 HLA class II binding peptide presented by the HLA class II binding molecule are selected. A first amino acid residue of the MAGE-3 HLA class II binding peptide is mutated to prepare a variant peptide. The binding of the variant peptide to HLA class II binding molecule and stimulation of the T cell are then determined, wherein binding of the variant peptide to the HLA class II binding molecule and stimulation of the T cell by the variant peptide presented by the HLA class II binding molecule indicates that the variant peptide is a functional variant. In preferred embodiments, the MAGE-3 HLA class II binding peptide comprises the amino acid sequence of SEQ ID NO:11, SEQ ID NO:41 or SEQ ID NO:42. More preferably, the MAGE-3 HLA class II-binding peptide is a peptide having the amino acid sequence of any of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. More preferably, the MAGE-3 HLA class II-binding peptide includes the amino acid sequence of SEQ ID NO:3, SEQ ID NO:4, SEQ ID NO:23, SEQ ID NO:34, SEQ ID NO:37 or SEQ ID NO:38. In certain embodiments, the methods further include the step of comparing the stimulation of the T cell by the MAGE-3 HLA class II binding peptide and the stimulation of the T cell by the functional variant as a determination of the effectiveness of the stimulation of the T cell by the functional variant.

The invention also provides pharmaceutical preparations containing any one or more of the medicaments described above or throughout the specification. Such pharmaceutical preparations can include pharmaceutically acceptable diluent carriers or excipients.

The use of the foregoing compositions, peptides and nucleic acids in the preparation of a medicament, particularly a medicament for treatment of cancer, also is provided.

These and other objects of the invention will be described in further detail in connection with the detailed description of the invention.

B6.37 (B6/37) EBV-B cells pulsed with the peptide RKVAELVHFLLLKYRA (MAGE-3$_{111\text{-}126}$, SEQ ID NO:3) or ELVHFLLLKYRAREPV MAGE-3$_{115\text{-}130}$, SEQ ID NO:4).

Figure 6:
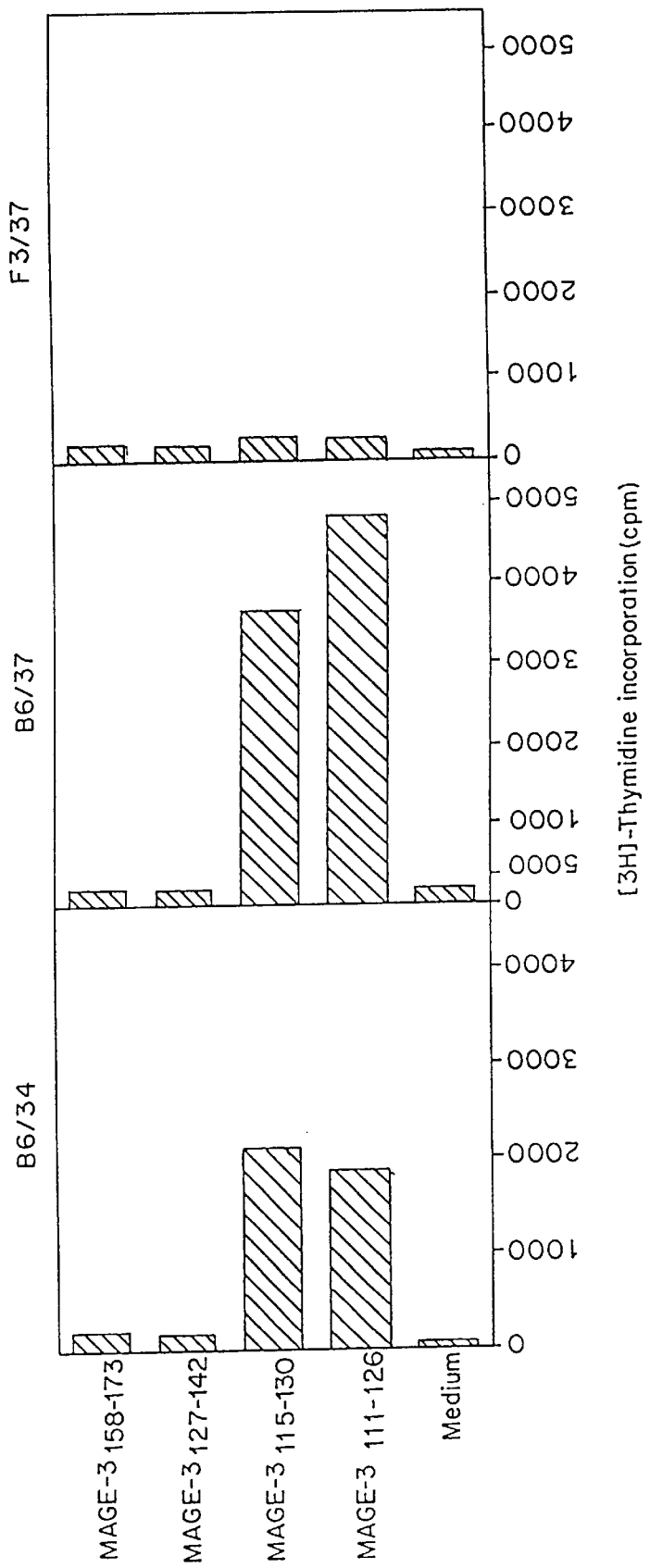

FIG. 6 is a graph which shows that autologous EBV-B cells pulsed with the peptide MAGE-3$_{111\text{-}126}$ or MAGE-3$_{115\text{-}130}$ induced the proliferation of clones 436/B6.34 (B6/34), 436/B6.37 (B6/37).

Figure 7:
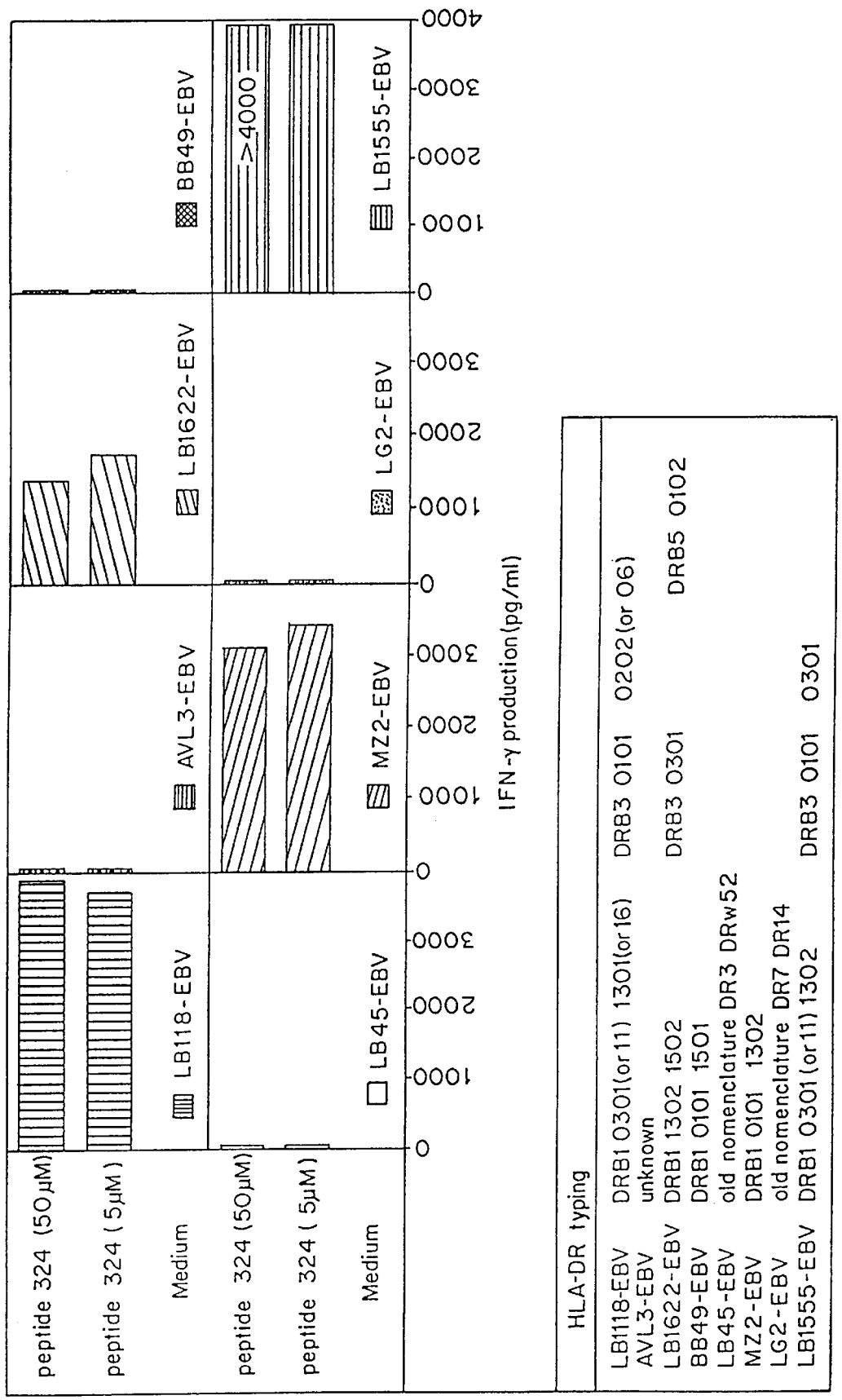

FIG. 7 is a graph which demonstrates that the response of CD4$^+$ clone 436/B6.37 B6/37) to peptide MAGE-3$_{115\text{-}130}$ is HLA-DRB1/1302 restricted.

Figure 8:
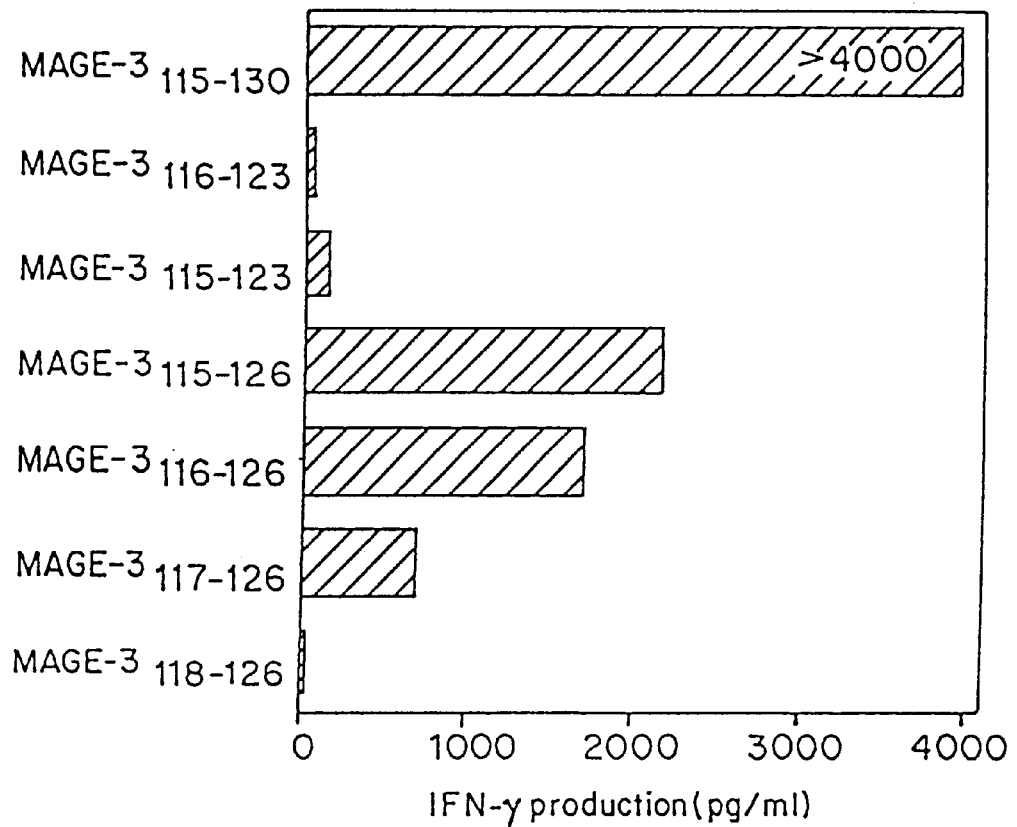

FIG. 8 is a graph which shows the reactivity of clone 436/B6.37 (B6/37) against autologous EBV-B cells pulsed with truncated peptides derived from MAGE-3$_{111\text{-}130}$.

FIG. 9 depicts the presentation of exogenous MAGE-3 processed by dendritic cells to clone 37.

Figure 10:
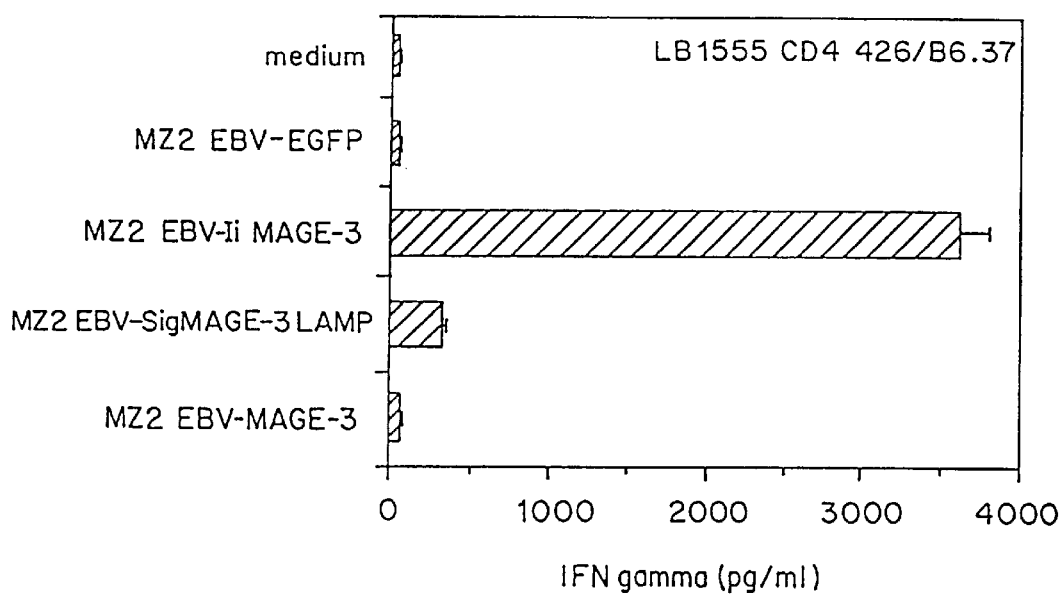

FIG. 10 shows the recognition of transduced MZ2 EBV by CD4 T cell clone 436/B6.37 (anti-MAGE-3.DR13).

Figure 11:
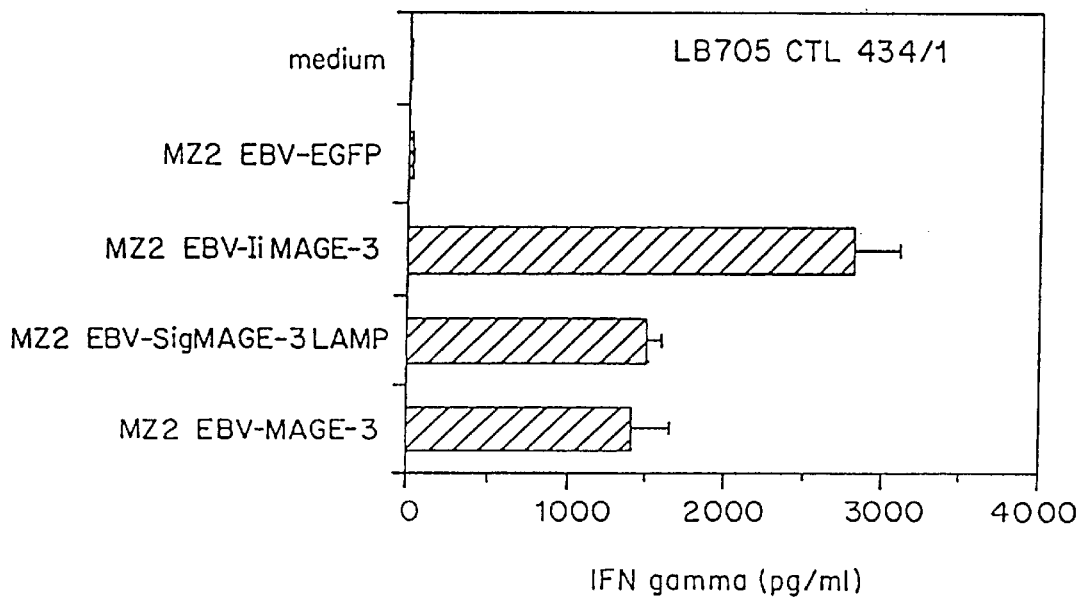

FIG. 11 shows the recognition of transduced MZ2 EBV by CTL clone 434/1 (anti-MAGE-3.A1).

Figure 12:
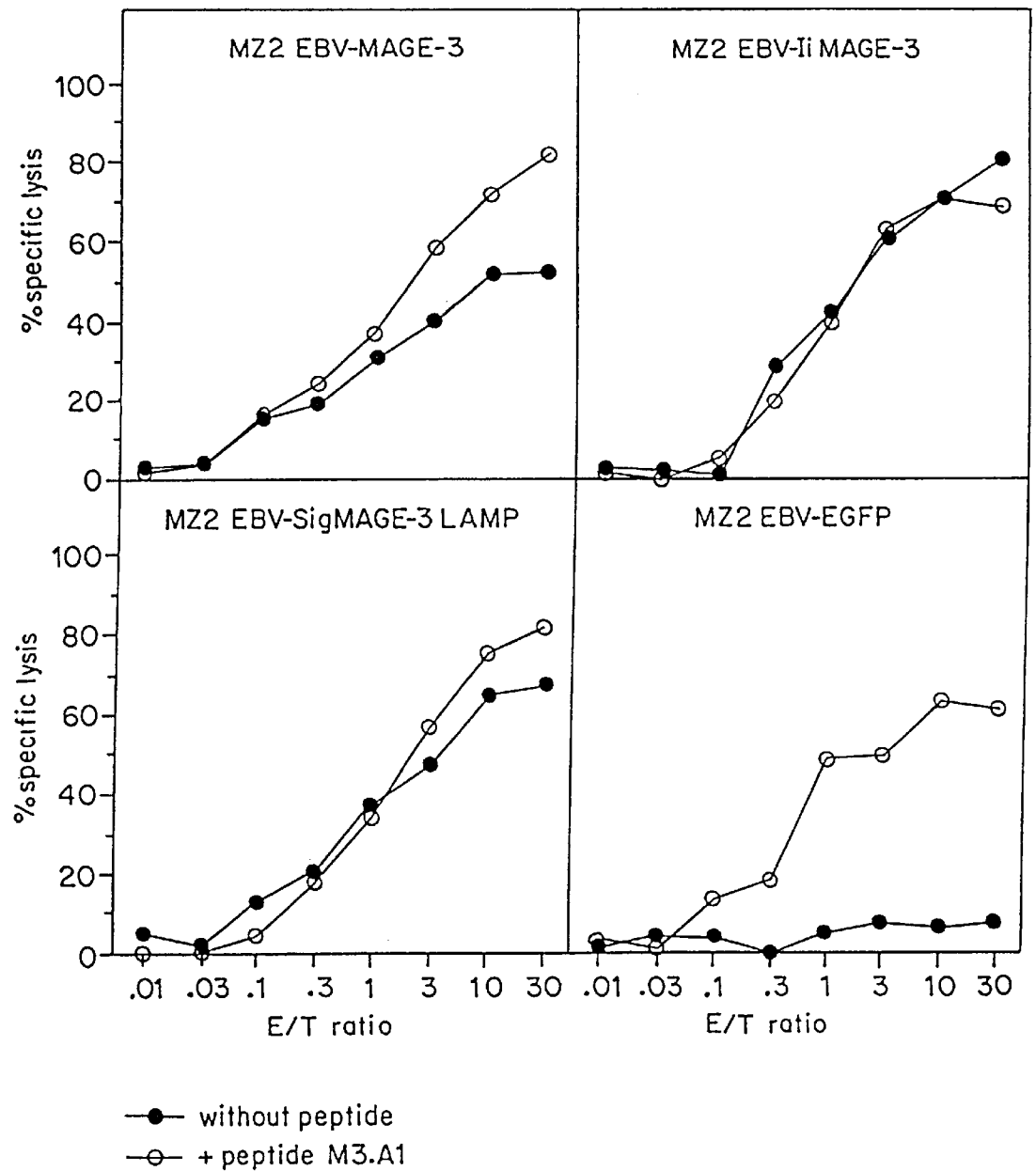

FIG. 12 shows the lysis of transduced MZ2 EBV by CTL434/1 (anti-MAGE-3.A1).

FIG. 13 shows the recognition of transduced MZ2-MEL.43 by CD4 T cell clone 436/B6.37 (anti-MAGE-3.DR13) and CTL clone 43411 (anti-MAGE-3.A1).

Figure 14:
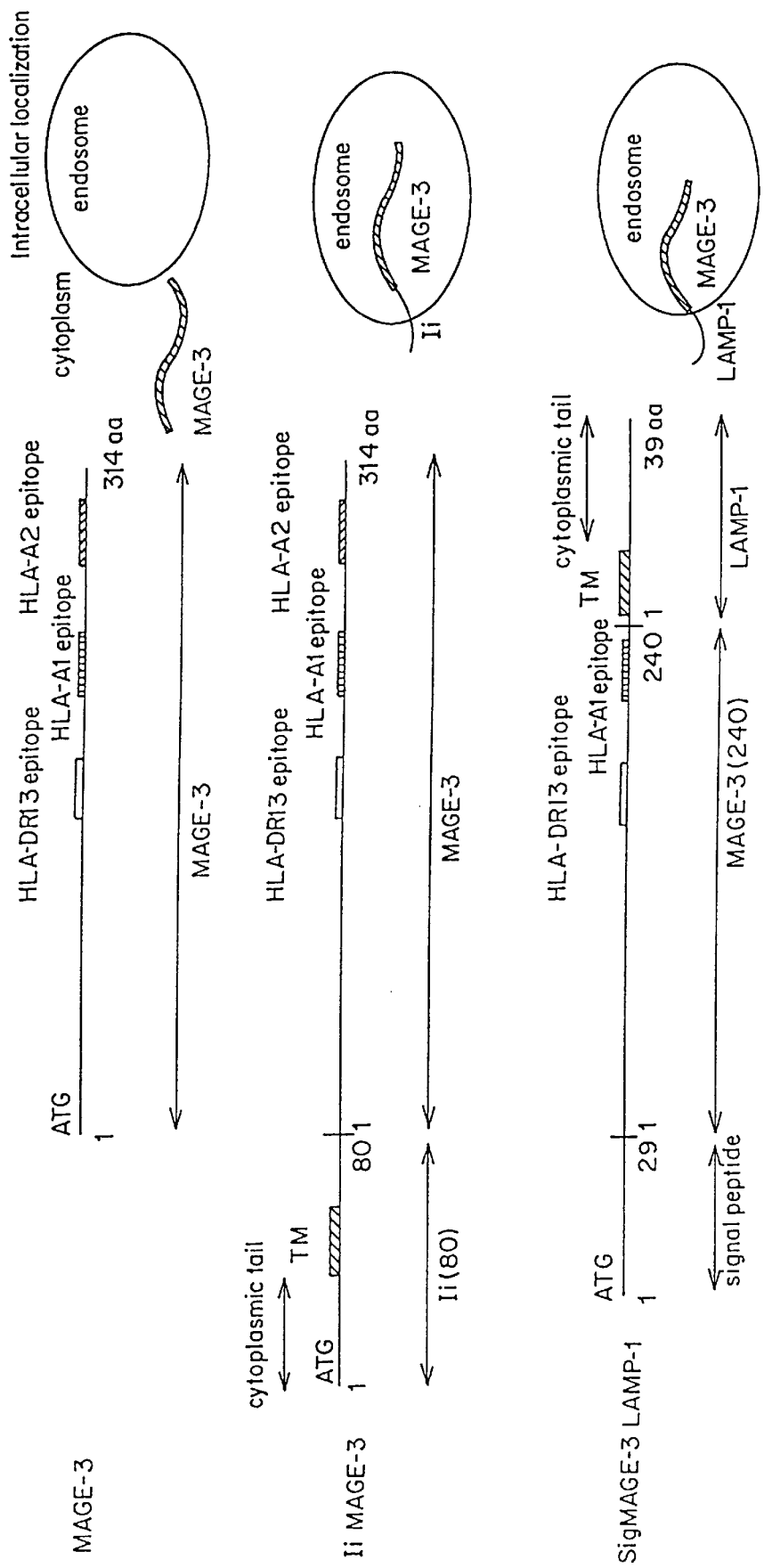

FIG. 14 is a schematic drawing of retroviral constructs of invariant chain (Ii) and LAMP-1 MAGE-3 fusion proteins.

FIG. 15 shows that clones 2 and 22 recognized a MAGE-3 derived peptide in association with HLA-DR.

DETAILED DESCRIPTION OF THE INVENTION

The invention provides isolated MAGE-3 peptides presented by HLA class II molecules, which peptides stimulate the proliferation and activation of CD4$^+$ T lymphocytes. Such peptides are referred to herein as "MAGE-3 HLA class II binding peptides", "HLA class II binding peptides" and "MHC class II binding peptides". Hence, one aspect of the invention is an isolated peptide which includes the amino acid sequence of SEQ ID NO:11, SEQ ID NO:41 or SEQ ID NO:42.

The examples below show the isolation of peptides which are MAGE-3 HLA class II binding peptides. These exemplary peptides are processed translation products of the nucleic acid of SEQ ID NO:1. As such, it will be appreciated by one of ordinary skill in the art that the translation products from which a MAGE-3 HLA class II binding peptide is processed to a final form for presentation may be of any length or sequence so long as they encompass the MAGE-3 HLA class II binding peptide. As demonstrated in the examples below, peptides or proteins as small as 10 amino acids and as large as the amino acid sequence of the MAGE-3 protein (SEQ ID NO:2) are appropriately processed, presented by HLA class II molecules and effective in stimulating CD4$^+$ T lymphocytes. MAGE-3 HLA class II binding peptides, such as the peptides of SEQ ID NO:11, SEQ ID NO:41 or SEQ ID NO:42 may have one, two, three, four, five, six, seven, eight, nine, ten, or more amino acids added to either or both ends. The antigenic portion of such a peptide is cleaved out under physiological conditions for presentation by HLA class II molecules. It is also well known in the art that HLA class II peptide length is variable between about 10 amino acids and about 30 amino acids (Engelhard, *Ann. Rev. Immunol.* 12:181–201, 1994). Most of the HLA class II binding peptides fall in to the length range of 12–19 amino acids. Nested sets of HLA class II binding peptides have been identified, wherein the peptides share a core sequence but have different amino acids at amino and/or carboxyl terminal ends (see, e.g., Chicz et al., *J. Exp. Med.* 178:27–47, 1993). Thus additional MAGE-3 HLA class II binding peptides, as well as MAGE family HLA class II binding peptides, can be identified by one of ordinary skill in the art according to the procedures described herein.

The procedures described in the Examples can be utilized to identify MAGE family HLA class II binding peptides. Thus, for example, one can load antigen presenting cells, such as dendritic cells of normal blood donors, with a recombinant MAGE protein (or a fragment thereof) by contacting the cells with the MAGE polypeptide or by introducing into the cells a nucleic acid molecule which directs the expression of the MAGE protein of interest. The antigen-presenting cells then can be used to induce in vitro the activation and proliferation of specific CD4 lymphocytes which recognize MAGE HLA class II binding peptides. The sequence of the peptides then can be determined as described in the Examples, e.g., by stimulating cells with peptide fragments of the MAGE protein used to stimulate the activation and proliferation of CD4 lymphocytes. Alternatively, one can load antigen presenting cells with peptides derived from a MAGE protein. For example, one can make predictions of peptide sequences derived from MAGE family proteins which are candidate HLA class II binding peptides based on the consensus amino acid sequences for binding HLA class II molecules. In this regard, see, e.g. International applications PCT/US96/03182 and PCT/US98/01373. Peptides which are thus selected can be used in the assays described herein for inducing specific CD4 lymphocytes and identification of peptides. Additional methods of selecting and testing peptides for HLA class II binding are well known in the art.

As noted above, the invention embraces functional variants of MAGE-3 HLA class II binding peptides. As used herein, a "functional variant" or "variant" of a HLA class II binding peptide is a peptide which contains one or more modifications to the primary amino acid sequence of a HLA class II binding peptide and retains the HLA class II and T cell receptor binding properties disclosed herein. Modifications which create a MAGE-3 HLA class II binding peptide functional variant can be made for example 1) to enhance a property of a MAGE-3 HLA class II binding peptide, such as peptide stability in an expression system or the stability of protein-protein binding such as HLA-peptide binding; 2) to provide a novel activity or property to a MAGE-3 HLA class II binding peptide, such as addition of an antigenic epitope or addition of a detectable moiety; or 3) to provide a different amino acid sequence that produces the same or similar T cell stimulatory properties. Modifications to MAGE-3 (as well as MAGE family) HLA class II binding peptides can be made to nucleic acids which encodes the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Variants also can be selected from libraries of peptides, which can be random peptides or peptides based on the sequence of the MAGE peptides including substitutions at one or more positions. For example, a peptide library can be used in competition assays with complexes of MAGE peptides bound to HLA class II molecules (e.g. dendritic cells loaded with MAGE peptide). Peptides which compete for binding of the MAGE peptide to the HLA class II molecule can be sequenced and used in other assays (e.g. CD4 lymphocyte proliferation) to determine suitability as MAGE peptide functional variants.

Modifications also embrace fusion proteins comprising all or part of a MAGE HLA class II binding peptide amino acid sequence, such as the invariant chain-MAGE-3 fusion proteins described herein. The invention thus embraces fusion proteins comprising MAGE-3 HLA class II binding peptides and endosomal targeting signals such as the human invariant chain (Ii). As is disclosed below, fusion of an endosomal targeting portion of the human invariant chain to MAGE-3 resulted in efficient targeting of MAGE-3 to the HLA class II peptide presentation pathway. An "endosomal targeting portion" of the human invariant chain or other targeting polypeptide is that portion of the molecule which, when fused or conjugated to a second polypeptide, increases endosomal localization of the second polypeptide. Thus endosomal targeting portions can include the entire sequence or only a small portion of a targeting polypeptide such as human invariant chain Ii. One of ordinary skill in the art can readily determine an endosomal targeting portion of a targeting molecule.

Surprisingly, fusion of an endosomal targeting portion of LAMP-1 protein did not significantly increase targeting of MAGE-3 to the HLA class II peptide presentation pathway. Therefore, the invention includes the unexpected finding that fusion proteins of MAGE-3 and human invariant chain Ii, but not LAMP-1, are efficiently targeted to the HLA class II peptide presentation pathway. Additional endosomal targeting signals can be identified by one of ordinary skill in the art, fused to MAGE-3 or a MAGE-3 HLA class II binding portion thereof, and tested for targeting to the HLA class II peptide presentation pathway using no more than routine experimentation.

The amino acid sequence of MAGE HLA class II binding peptides may be of natural or non-natural origin, that is, they may comprise a natural MAGE HLA class II binding peptide molecule or may comprise a modified sequence as long as the amino acid sequence retains the ability to stimulate helper T cells when presented and retains the property of binding to an HLA class II molecule such as an HLA DRB1/13 molecule. For example, MAGE-3 HLA class II binding peptides in this context may be fusion proteins including a MAGE-3 HLA class II binding peptide and unrelated amino acid sequences, synthetic peptides of amino acid sequences shown in SEQ ID Nos:3, 4, 9, 10 and 11, labeled peptides, peptides isolated from patients with a MAGE:3 expressing cancer, peptides isolated from cultured cells which express MAGE-3, peptides coupled to nonpeptide molecules (for example in certain drug delivery systems) and other molecules which include the amino acid sequence of SEQ ID NO:11, SEQ ID NO:41 or SEQ ID NO:42.

Preferably, MAGE HLA class II binding peptides are non-hydrolyzable. To provide such peptides, one may select MAGE HLA class II binding peptides from a library of non-hydrolyzable peptides, such as peptides containing one or more D-amino acids or peptides containing one or more non-hydrolyzable peptide bonds linking amino acids. Alternatively, one can select peptides which are optimal for inducing CD4$^+$ T lymphocytes and then modify such peptides as necessary to reduce the potential for hydrolysis by proteases. For example, to determine the susceptibility to proteolytic cleavage, peptides may be labeled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of a MAGE-3 HLA class II binding peptide with the known cleavage site specificity of a panel of proteases. Based on the results of such assays, individual peptide bonds which are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include -psi[CH$_2$NH]-reduced amide peptide bonds, -psi[COCH$_2$]-ketomethylene peptide bonds, -psi[CH(CN)NH]-(cyanomethylene)amino peptide bonds, -psi[CH$_2$CH(OH)]-hydroxyethylene peptide bonds, -psi[CH$_2$O] peptide bonds, and -psi[CH$_2$S]-thiomethylene peptide bonds.

Nonpeptide analogs of peptides, e.g., those which provide a stabilized structure or lessened biodegradation, are also contemplated. Peptide mimetic analogs can be prepared based on a selected MAGE-3 HLA class II binding peptide by replacement of one or more residues by nonpeptide moieties. Preferably, the nonpeptide moieties permit the peptide to retain its natural conformation, or stabilize a preferred, e.g., bioactive, confirmation. Such peptides can be tested in molecular or cell-based binding assays to assess the effect of the substitution(s) on conformation and/or activity. One example of methods for preparation of nonpeptide mimetic analogs from peptides is described in Nachman et al., Regul. Pept. 57:359–370 (1995). Peptide as used herein embraces all of the foregoing.

If a variant involves a change to an amino acid of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 or SEQ ID NO:39., functional variants of the MAGE-3 HLA class II binding peptide having conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Other methods for identifying functional variants of the MAGE-3 HLA class II binding peptides are provided in a published PCT application of Strominger and Wucherpfennig (PCT/US96/03182). These methods rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of the residues valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; and that the residue at the fifth position must be lysine.

Sequence motifs for MAGE-3 HLA class II binding peptide: functional variants can be developed by analysis of the binding domains or binding pockets of major histocompatibility complex HLA-DR proteins and/or the T cell receptor ("TCR") contact points of the MAGE-3 HLA class II binding peptides disclosed herein. By providing a detailed structural analysis of the residues involved in forming the HLA class II binding pockets, one is enabled to make predictions of sequence motifs for binding of MAGE peptides to any of the HLA class II proteins.

Using these sequence motifs as search, evaluation, or design criteria, one is enabled to identify classes of peptides (e.g. MAGE HLA class II binding peptides, particularly the MAGE-3 peptides disclosed herein, and functional variants thereof) which have a reasonable likelihood of binding to a particular HLA molecule and of interacting with a T cell receptor to induce T cell response. These peptides can be synthesized and tested for activity as described herein. Use of these motifs, as opposed to pure sequence homology (which excludes many peptides which are antigenically similar but quite distinct in sequence) or sequence homology with unlimited "conservative" substitutions (which admits many peptides which differ at critical highly conserved sites), represents a method by which one of ordinary skill in the art can evaluate peptides for potential application in the treatment of disease.

The Strominger and Wucherpfennig PCT application, and references cited therein, all of which are incorporated by reference, describe the HLA class II and TCR binding pockets which contact residues of an HLA class II peptide. By keeping the residues which are likely to bind in the HLA class II and/or TCR binding pockets constant or permitting only specified substitutions, functional variants of MAGE HLA class II binding peptides can be prepared which retain binding to HLA class II and T cell receptor.

Thus methods for identifying additional MAGE family HLA class II peptides, in particular MAGE-3 HLA class II binding peptides, and functional variants thereof, are provided. In general, any MAGE protein can be subjected to the analysis noted above, peptide sequences selected and the tested as described herein. With respect to MAGE-3, for example, the methods include selecting a MAGE-3 HLA class II binding peptide, an HLA class II binding molecule which binds the MAGE-3 HLA class II binding peptide, and a T cell which is stimulated by the MAGE-3 HLA class II binding peptide presented by the HLA class II binding molecule. In preferred embodiments, the MAGE-3 HLA class II binding peptide comprises the amino acid sequence of SEQ ID NO:11, SEQ ID NO:41, SEQ ID NO:42. More preferably, the peptide consists of the amino acid sequence of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39. A first amino acid residue of the MAGE-3 HLA class II binding peptide is mutated to prepare a variant peptide. The amino acid residue can be mutated according to the principles of HLA and T cell receptor contact points set forth in the Strominger and Wucherpfennig PCT application described above. Any method for preparing variant peptides can be employed, such as synthesis of the variant peptide, recombinantly producing the variant peptide using a mutated nucleic acid molecule, and the like.

The binding of the variant peptide to HLA class II binding molecule and stimulation of the T cell are then determined according to standard procedures. For example, as exemplified below, the variant peptide can be contacted with an antigen presenting cell which contains the HLA class II molecule which binds the MAGE-3 peptide to form a complex of the variant peptide and antigen presenting cell. This complex can then be contacted with a T cell which recognizes the MAGE-3 HLA class II binding peptide presented by the HLA class II binding molecule. T cells can be obtained from a patient having a condition characterized by expression of MAGE-3. Recognition of variant peptides by the T cells can be determined by measuring an indicator of T cell stimulation such as TNF or IFNγ production. Similar procedures can be carried out for identification and characterization of other MAGE family HLA class II binding peptides.

Binding of a variant peptide to the HLA class II binding molecule and stimulation of the T cell by the variant peptide presented by the HLA class II binding molecule indicates that the variant peptide is a functional variant. The methods also can include the step of comparing the stimulation of the T cell by the MAGE-3 HLA class II binding peptide and the stimulation of the T cell by the functional variant as a determination of the effectiveness of the stimulation of the T cell by the functional variant. By comparing the functional variant with the MAGE-3 HLA class II binding peptide, peptides with increased T cell stimulatory proterties can be prepared.

Variants of the MAGE-3 HLA class II binding peptides prepared by any of the foregoing methods can be sequenced, if necessary, to determine the amino acid sequence and thus deduce the nucleotide sequence which encodes such variants.

Also a part of the invention are those nucleic acid sequences which code for a MAGE HLA class II binding peptides or variant thereof and other nucleic acid sequences which hybridize to a nucleic acid molecule consisting of the above described nucleotide sequences, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers to hybridization at 65° C. in hybridization buffer (3.5×SSC, 0.02% Ficoll, 0.02% Polyvinyl pyrolidone, 0.02% Bovine Serum Albumin, 25 mM $NaH_2PO_4$ (pH7), 0.5% SDS, 2 mM EDTA). SSC is 0.15 M Sodium Chloride/0.15 M Sodium Citrate, pH 7; SDS is Sodium Dodecyl Sulphate; and EDTA is Ethylene diaminetetraacetic acid. After hybridization, the membrane upon which the DNA is transferred is washed at 2×SSC. at room temperature and then at 0.1×SSC/0.1×SDS at 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids encoding the MAGE HLA class II binding peptides of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 50% amino acid identity and/or at least 40% nucleotide identity to the amino acid sequence of a MAGE-3 HLA class II binding peptide (such as SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID:NO:39) or nucleic acids which encode such a peptide, respectively. In some instances homologs and alleles will share at least 50% nucleotide identity and/or at least 65% amino acid identity and in still other instances will share at least 60% nucleotide identity and/or at least 75% amino acid identity. Complements of the foregoing nucleic acids also are embraced by the invention.

In screening for nucleic acids which encode a MAGE HLA class II binding peptide, a is nucleic acid hybridization such as a Southern blot or a Northern blot may be performed using the foregoing conditions, together with a $^{32}P$ probe. After washing the membrane to which DNA encoding a MAGE HLA class II binding peptide was finally transferred, the membrane can be placed against X-ray film to detect the radioactive signal.

The invention also includes the use of nucleic acid sequences which include alternative codons that encode the same amino acid residues of the MAGE HLA class II binding peptides. For example, as disclosed herein, the peptide RKVAELVHFLLLKYRA (SEQ ID NO:3) is a MAGE-3 HLA class II binding peptide. The leucine residues (amino acids No. 6, 11 and 12 of SEQ ID NO:3) can be encoded by the codons CUA, CUC, CUG, CUU, UUA and UUG. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues comprising the MAGE-3 HLA class II binding peptide of SEQ ID NO:3 include: CGA, CGC, CGG, CGT, AGA and AGG (arginine codons); AAA and AAG (lysine codons); GUA, GUC, GUG and GUU (valine codons); GAA and GAG (glutamine codons); CAC and CAU (histidine codons); UUC and UUU (phenylalanine codons) and UAC and UAU (tyrosine codons). Other amino acid residues may be encoded similarly by multiple nucleotide sequences. Thus, the invention embraces degenerate nucleic acids that differ from the native MAGE HLA class II binding peptide encoding nucleic acids in codon sequence due to the degeneracy of the genetic code.

It will also be understood that the invention embraces the use of the sequences in expression vectors, as well as to transfect host cells and cell lines, be these prokaryotic (e.g., E. coli), or eukaryotic (e.g., dendritic cells, CHO cells, COS cells, yeast expression systems and recombinant baculovirus expression in insect cells). The expression vectors require that the pertinent sequence, i.e., those described supra, be operably linked to a promoter. As it has been found that human HLA-DRB1/1302 molecules present a MAGE-3 HLA class II binding peptide, the expression vector may also include a nucleic acid sequence coding for an HLA-DRB1/13 molecule. (For other MAGE HLA class II binding peptides, different HLA molecules can be used.) In a situation where the vector contains both coding sequences, it can be used to transfect a cell which does not normally express either one. The MAGE-3 HLA class II binding peptide coding sequence may be used alone, when, e.g. the host cell already expresses an HLA-DRB1/13 molecule. Of course, there is no limit on the particular host cell which can be used as the vectors which contain the two coding sequences may be used in host cells which do not express HLA-DRB1/13 molecules if desired, and the nucleic acid coding for the MAGE-3 HLA class II binding peptide can be used in antigen presenting cells which express an HLA-DRB1/13 molecule. As used herein, "an HLA-DRB1/13 molecule" includes the subtypes DRB1*1301, DRB1*1302, DRB1*13031, DRB1*13032, DRB1*1304, DRB1*1305, DRB1*1306, DRB1*1307, DRB1*1308, DRB1*1309, DRB1*1310, DRB1*1311, DRB1*1312, DRB1*1314, DRB1*1315, DRB1*1316, DRB1*1317, DRB1*1318, DRB1*1319, DRB1*1320, DRB1*1321, DRB1*1322, DRB1*1323 and DRB1*1324. An HLA-DRB1/13 molecule also includes the subtypes which can be found in Bodmer et al., *Tissue Antigens* 49:297, 1996.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or after integration into the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

Preferably the expression vectors contain sequences which target a MAGE family polypeptide, e.g. MAGE-3, or a HLA class II binding peptide derived therefrom, to the endosomes of a cell in which the protein or peptide is expressed. HLA class II molecules contain an invariant chain (Ii) which impedes binding of other molecules to the HLA class II molecules. This invariant chain is cleaved in endosomes, thereby permitting binding of peptides by HLA class II molecules. Therefore it is preferable that the MAGE-3 HLA class II binding peptides and precursors thereof (e.g. the MAGE-3 protein) are targeted to the endosome, thereby enhancing MAGE-3 HLA class II binding peptide binding to HLA class II molecules. Targeting signals for directing molecules to endosomes are known in the art and these signals conveniently can be incorporated in expression vectors such that fusion proteins which contain the endosomal targeting signal are produced. Sanderson et al. (*Proc. Nat'l. Acad Sci. USA* 92:7217–7221, 1995), Wu et al. (*Proc. Nat'l. Acad. Sci. USA* 92:11671–11675, 1995) and Thomson et al (*J. Virol.* 72:2246–2252, 1998) describe endosomal targeting signals (including invariant chain Ii and lysosomal-associated membrane protein LAMP-1) and their use in directing antigens to endosomal and/or lysosomal cellular compartments. As disclosed in the Examples, invariant chain-MAGE-3 fusion proteins are preferred.

Endosomal targeting signals such as invariant chain also can be conjugated to MAGE-3 protein or peptides by non-peptide bonds (i.e. not fusion proteins) to prepare a conjugate capable of specifically targeting MAGE-3. Specific examples of covalent bonds include those wherein bifunctional cross-linker molecules are used. The cross-linker molecules may be homobifunctional or heterobifunctional, depending upon the nature of the molecules to be conjugated. Homobifunctional cross-linkers have two identical reactive groups. Heterobifunctional cross-linkers are defined as having two different reactive groups that allow for sequential conjugation reaction. Various types of commercially available cross-linkers are reactive with one or more of the following groups; primary amines, secondary amines, sulfhydryls, carboxyls, carbonyls and carbohydrates. One of ordinary skill in the art will be able to ascertain without undue experimentation the preferred molecule for linking the endosomal targeting moiety and MAGE-3 peptide or protein, based on the chemical properties of the molecules being linked and the preferred characteristics of the bond or bonds.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a MAGE-3 HLA class II binding peptide. That heterologous DNA (RNA) is placed under operable control of transcriptional elements to permit the expression of the heterologous DNA in the host cell. As described herein, such expression constucts optionally also contain nucleotide sequences which encode endosomal targeting signals, preferably human invariant chain or a targetting fragment thereof Preferred systems for mRNA expression in mammalian cells are those such as pRc/CMV (available from Invitrogen, Carlsbad, Calif.) that contain a selectable marker such as a gene that confers G418 resistance (which facilitates the selection of. stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer,* 67:303–310, 1996).

The invention also embraces so-called expression kits, which allow the artisan to prepare a desired expression vector or vectors. Such expression kits include at least separate portions of at least two of the previously discussed materials. Other components may be added, as desired.

The invention as described herein has a number of uses, some of which are described herein. The following uses are described for MAGE-3 HLA class II binding peptides but are equally applicable to use of other MAGE family HLA class II binding peptides. First, the invention permits the artisan to diagnose a disorder characterized by expression of a MAGE-3 HLA class II binding peptide. These methods involve determining expression of a MAGE-3 HLA class II binding peptide, or a complex of a MAGE-3 HLA class III binding peptide and an HLA class II molecule in a biological sample. The expression of a peptide or complex of peptide and HLA class II molecule can be determined by assaying with a binding partner for the peptide or complex, such as an antibody.

The invention also permits the artisan to treat a subject having a disorder characterized by expression of a MAGE-3 HLA class II binding peptide. Treatments include administering an agent which enriches in the subject a complex of a MAGE-3 HLA class II binding peptide and an HLA class II molecule, and administering CD4$^+$ T lymphocytes which are specific for such complexes. Agents useful in the foregoing treatments include MAGE-3 HLA class II binding peptides and functional variants thereof, endosome-targeted fusion proteins which include such MAGE-3 peptides, nucleic acids which express such proteins and peptides (including viruses which contain the nucleic acids), complexes of such peptides and HLA class II binding molecules (e.g. HLA DRB1/1302), antigen presenting cells bearing complexes of a MAGE-3 HLA class II binding peptide and an HLA class II binding molecule, and the like. The invention also permits an artisan to selectively enrich a population of T lymphocytes for CD4+ T lymphocytes specific for a MAGE-3 HLA class II binding peptide.

The isolation of the MAGE-3 HLA class II binding peptides also makes it possible to isolate nucleic acids which encode the MAGE-3 HLA class II binding peptides. Nucleic acids can be used to produce in vitro or in prokaryotic or eukaryotic host cells the MAGE-3 HLA class II binding peptides. A variety of methodologies well-known to the skilled practitioner can be utilized to obtain isolated MAGE-3 HLA class II binding peptides. For example, an expression vector may be introduced into cells to cause production of the peptides. In another method, mRNA transcripts may be microinjected or otherwise introduced into cells to cause production of the encoded peptides. Translation of mRNA in cell-free extracts such as the reticulocyte lysate system also may be used to produce peptides. Peptides comprising the MAGE-3 HLA class II binding peptide of the invention may also be synthesized in vitro. Those skilled in the art also can readily follow known methods for isolating peptides in order to obtain isolated MAGE-3 HLA class II binding peptides. These include, but are not limited to, immunochromotography, HPLC, size-exclusion chromatography, ion-exchange chromatography and immune-affinity chromatography.

These isolated MAGE-3 HLA class II binding peptides, proteins which include such peptides, or complexes of the peptides and HLA class II molecules, such as an HLA-DRB1/13 molecule, may be combined with materials such as adjuvants to produce vaccines useful in treating disorders characterized by expression of the MAGE-3 HLA class II binding peptide. In addition, vaccines can be prepared from cells which present the MAGE-3 HLA class II binding peptide/HLA complexes on their surface, such as dendritic cells, B cells, non-proliferative transfectants, etcetera. In all cases where cells are used as a vaccine, these can be cells transfected with coding sequences for one or both of the components necessary to stimulate CD4+ lymphocytes, or be cells which already express both molecules without the need for transfection. For example, autologous antigen presenting cells can be isolated from a patient and treated to obtain cells which present MAGE-3 epitopes in association of HLA class I and HLA class II molecules. These cells would be capable of stimulating both CD4+ and CD8+ cell responses. Such antigen presenting cells can be obtained by infecting dendritic cells with recombinant viruses encoding an Ii.MAGE-3 fusion protein. Dendritic cells also can be loaded with HLA class I and HLA class II epitopes.

Vaccines also encompass naked DNA or RNA, encoding a MAGE-3 HLA class II binding peptide or precursor thereof, which may be produced in vitro and administered via injection, particle bombardment, nasal aspiration and other methods. Vaccines of the "naked nucleic acid" type have been demonstrated to provoke an immunological response including generation of CTLs specific for the peptide encoded by the naked nucleic acid (*Science* 259:1745–1748, 1993). Vaccines also include nucleic acids packaged in a virus, liposome or other particle, including polymeric particles useful in drug delivery.

The immune response generated or enhanced by any of the treatments described herein can be monitored by various methods known in the art. For example, the presence of T cells specific for a given antigen can be detected by direct labeling of T cell receptors with soluble fluorogenic MHC molecule tetramers which present the antigenic peptide (Altman et al., *Science* 274:94–96, 1996; Dunbar et al., *Curr. Biol.* 8:413–416, 1998). Briefly, soluble MHC class I molecules are folded in vitro in the presence of β2-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio of 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein. The use of MHC class II molecules as tetramers was recently demonstrated by Crawford et al. (*Immunity* 8:675–682, 1998). Multimeric soluble MHC class II molecules were complexed with a covalently attached peptide. The class II tetramers were shown to bind with appropriated specificity and affinity to specific T cells. Thus tetramers can be used to monitor both CD4+ and CD8+ cell responses to vaccination protocols.

The MAGE-3 HLA class II binding peptide, as well as complexes of MAGE-3 HLA class II binding peptide and HLA molecule, also may be used to produce antibodies, using standard techniques well known to the art. Standard reference works setting forth the general principles of antibody production include Catty, D., *Antibodies, A Practical Approach*, Vol. 1, IRL Press, Washington DC (1988); Klein, J., *Immunology: The Science of Cell-Non-Cell Discrimination*, John Wiley and Sons, New York (1982); Kennett, R., et al., *Monoclonal Antibodies, Hybridoma, A New Dimension In Biological Analyses*, Plenum Press, New York (1980); Campbell, A., *Monoclonal Antibody Technology*, in *Laboratory Techniques and Biochemistry and Molecular Biology*, Vol. 13 (Burdon, R. et al. EDS.), Elsevier Amsterdam (1984); and Eisen, H. N., *Microbiology*, third edition, Davis, B. D. et al. EDS. (Harper & Rowe, Philadelphia (1980).

The antibodies of the present invention thus are prepared by any of a variety of methods, including administering protein, fragments of protein, cells expressing the protein or fragments thereof and an appropriate HLA class II molecule, and the like to an animal to induce polyclonal antibodies. The production of monoclonal antibodies is according to techniques well known in the art. As detailed herein, such antibodies may be used for example to identify tissues expressing protein or to purify protein. Antibodies also may be coupled to specific labeling agents for imaging or to antitumor agents, including, but not limited to, methotrexate, radioiodinated compounds, toxins such as ricin, other cytostatic or cytolytic drugs, and so forth. Antibodies prepared according to the invention also preferably are specific for the peptide/HLA complexes described herein.

When "disorder" or "condition" is used herein, it refers to any pathological condition where the MAGE-3 HLA class II binding peptide is expressed. Such disorders include cancers, such as melanomas, squamous cell carcinomas of the head, neck, lung or esophagus, colorectal carcinomas, osteosarcomas, neuroblastomas, non-squamous cell carcinomas of the head or neck, ovarian tumors, lymphocytic leukemias, bladder carcinomas, prostate carcinomas, etc.

Some therapeutic approaches based upon the disclosure are premised on inducing a response by a subject's immune system to MAGE HLA class II binding peptide presenting cells. One such approach is the administration of autologous CD4+ T cells specific to the complex of MAGE-3 HLA class II binding peptide and an HLA class II molecule to a subject with abnormal cells of the phenotype at issue. It is within the skill of, the artisan to develop such CD4+ T cells in vitro. Generally, a sample of cells taken from a subject, such as blood cells, are contacted with a cell presenting the complex and capable of provoking CD4+ T lymphocytes to proliferate. The target cell can be a transfectant, such as a COS cell, or an antigen presenting cell bearing HLA class II molecules, such as dendritic cells or B cells. These transfectants present the desired complex of their surface and, when combined with a CD4+ T lymphocyte of interest, stimulate its proliferation. COS cells are widely available, as are other suitable host cells. Specific production of CD4+ T lymphocytes is described below. The clonally expanded autologous CD4+ T lymphocytes then are administered to the subject. The CD4+ T lymphocytes then stimulate the subject's immune response, thereby achieving the desired therapeutic goal.

The foregoing therapy assumes that at least some of the subject's abnormal cells present the relevant HLA/peptide complex. This can be determined very easily, as the art is very familiar with methods for identifying cells which present a particular HLA molecule, as well as how to identify cells expressing DNA of the pertinent sequences, in this case a MAGE-3 sequence.

The foregoing therapy is not the only form of therapy that is available in accordance with the invention. CD4+ T lymphocytes can also be provoked in vivo, using a number of approaches. One approach is the use of non-proliferative cells expressing the complex. The cells used in this approach may be those that normally express the complex, such as dendritic cells or cells transfected with one or both of the genes necessary for presentation of the complex. Chen et al., (Proc. Natl. Acad. Sci. USA 88: 110–114, 1991) exemplifies this approach, showing the use of transfected cells expressing HPV-E7 peptides in a therapeutic regime. Various cell types may be used. Similarly, vectors carrying one or both of the genes of interest may be used. Viral or bacterial vectors are especially preferred. For example, nucleic acids which encode a MAGE-3 HLA class II binding peptide may be operably linked to promoter and enhancer sequences which direct expression of the MAGE-3 HLA class II binding peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding MAGE-3 HLA class II binding peptides. Nucleic acids encoding a MAGE-3 HLA class II binding peptide also may be inserted into a retroviral genome, thereby facilitating integration of the nucleic acid into the genome of the target tissue or cell type. In these systems, the gene of interest is carried by a microorganism, e.g., a Vaccinia virus, poxviruses in general, adenovirus, herpes simplex virus, retrovirus or the bacteria BCG, and the materials de facto "infect" host cells. The cells which result present the complex of interest, and are recognized by autologous CD4+ T cells, which then proliferate.

A similar effect can be achieved by combining a MAGE HLA class II binding peptide with an adjuvant to facilitate incorporation into HLA class II presenting cells in vivo. If larger than the HLA class II binding portion, the MAGE-3 HLA class II binding peptide can be processed if necessary to yield the peptide partner of the HLA molecule while the TRA is presented without the need for further processing. Generally, subjects can receive an intradermal injection of an effective amount of the MAGE-3 HLA class II binding peptide. Initial doses can be followed by booster doses, following immunization protocols standard in the art.

A preferred method for facilitating incorporation of MAGE-3 HLA class II binding peptides into HLA class II presenting cells is by expressing in the presenting cells a polypeptide which includes an endosomal targeting signal fused to a MAGE-3 polypeptide which includes the class II binding peptide. Particularly preferred are MAGE-3 fusion proteins which contain human invariant chain Ii.

Any of the foregoing compositions or protocols can include also MAGE HLA class I binding peptides for induction of a cytolytic T lymphocyte response. For example, as demonstrated below, the MAGE-3 protein can be processed in a cell to produce both HLA class I and HLA class II responses. Several such peptides have been described in U.S. Pat. Nos. 5,585,461 and 5,591,430 as well as by Gaugler et al. (J. Exp. Med. 179:921–930, 1994), van der Bruggen et al. (Eur. J. Immonol. 24:3038–3043, 1994), and Herman et al. (Immunogenetics 43:377–383, 1996). By administering MAGE-3 peptides which bind HLA class I and class II molecules (or nucleic acid encoding such peptides); an improved immune response may be provided by inducing both T helper cells and T killer cells.

In addition, non-MAGE-3 tumor associated peptides also can be administered to increase immune response via HLA class I and/or class II. It is well established that cancer cells can express more that one tumor associated gene. It is within the scope of routine experimentation for one of ordinary skill in the art to determine whether a particular subject expresses additional tumor associated genes, and then include HLA class I and/or HLA class II binding peptides derived from expression products of such genes in: the foregoing MAGE-3 compositions and vaccines.

Especially preferred are nucleic acids encoding a series of epitopes, known as "polytopes". The epitopes can be arranged in sequential or overlapping fashion (see, e.g., Thomson et al., Proc. Natl. Acad Sci. USA 92:5845–5849, 1995; Gilbert et al., Nature Biotechnol. 15:1280–1284, 1997), with or without the natural flanking sequences, and can be separated by unrelated linker sequences if desired. The polytope is processed to generated individual epitopes which are recognized by the immune system for generation of immune responses.

Thus, for example, MAGE-3 HLA class II binding peptides can be combined with peptides from other tumor rejection antigens (e.g. by preparation of hybrid nucleic acids or polypeptides) and with MAGE-3 HLA class I binding peptides (some of which are listed below) to form "polytopes". Exemplary tumor associated peptide antigens that can be administered to induce or enhance an immune response are derived from tumor associated genes and encoded proteins including MAGE-1, MAGE-2, MAGE-3, MAGE-4, MAGE-5, MAGE-6, MAGE-7, MAGE-8, MAGE-9, MAGE-10, MAGE-11, MAGE-12, MAGE-13 GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2); MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1 and CT-7. For example, antigenic peptides characteristic of tumors include those listed in Table I below.

TABLE I

Exemplary Antigens

| Gene | MHC | Peptide | Position | SEQ ID NO: |
| --- | --- | --- | --- | --- |
| MAGE-1 | HLA-A1 | EADPTGHSY | 161–169 | 45 |
|  | HLA-Cw16 | SAYGEPRKL | 230–238 | 46 |
| MAGE-3 | HLA-A1 | EVDPIGHLY | 168–176 | 47 |
|  | HLA-A2 | FLWGPRALV | 271–279 | 48 |
|  | HLA-B44 | MEVDPIGHLY | 167–176 | 49 |
| BAGE | HLA-Cw16 | AARAVFLAL | 2–10 | 50 |
| GAGE-1,2 | HLA-Cw16 | YRPRPRRY | 9–16 | 51 |
| RAGE | HLA-B7 | SPSSNRIRNT | 11–20 | 52 |
| GnT-V | HLA-A2 | VLPDVFIRC(V) | 2–10/11 | 53, 54 |
| MUM-1 | HLA-B44 | EEKLIVVLF | exon 2/intron | 55 |
|  |  | EEKLSVVLF (wild type) |  | 56 |
| CDK4 | HLA-A2 | ACDPHSGHFV | 23–32 | 57 |
|  |  | ARDPHSGHFV (wild type) |  | 58 |
| β-catenin | HLA-A24 | SYLDSGIHF | 29–37 | 59 |
|  |  | SYLDSGIHS (wild type) |  | 60 |
| Tyrosinase | HLA-A2 | MLLAVLYCL | 1–9 | 61 |
|  | HLA-A2 | YMNGTMSQV | 369–377 | 62 |
|  | HLA-A2 | YMDGTMSQV | 369–377 | 78 |
|  | HLA-A24 | AFLPWHRLF | 206–214 | 63 |
|  | HLA-B44 | SEIWRDIDF | 192–200 | 64 |
|  | HLA-B44 | YEIWRDIDF | 192–200 | 65 |
|  | HLA-DR4 | QNILLSNAPLGPQFP | 56–70 | 66 |
|  | HLA-DR4 | DYSYLQDSDPDSFQD | 448–462 | 67 |
| Melan-A$^{MART-1}$ | HLA-A2 | (E)AAGIGILTV | 26/27–35 | 68, 69 |
|  | HLA-A2 | ILTVILGVL | 32–40 | 70 |
| gp100$^{Pmel117}$ | HLA-A2 | KTWGQYWQV | 154–162 | 71 |
|  | HLA-A2 | ITDQVPFSV | 209–217 | 72 |
|  | HLA-A2 | YLEPGPVTA | 280–288 | 73 |
|  | HLA-A2 | LLDGTATLRL | 457–466 | 74 |
|  | HLA-A2 | VLYRYGSFSV | 476–485 | 75 |
| PRAME | HLA-A24 | LYVDSLFFL | 301–309 | 76 |
| MAGE-6 | HLA-Cw16 | KISGGPRJSYPL | 292–303 | 77 |
| NY-ESO-1 | HLA-A2 | SLLMWITQCFL | 157–167 | 79 |
|  | HLA-A2 | SLLMWITQC | 157–165 | 80 |
|  | HLA-A2 | QLSLLMWIT | 155–163 | 81 |

Other examples of HLA class I and HLA class II binding peptides will be known to one of ordinary skill in the art (for example, see Coulie, *Stem Cells* 13:393–403, 1995), and can be used in the invention in a like manner as those disclosed herein. One of ordinary skill in the art can prepare polypeptides comprising one or more MAGE-3 peptides and one or more of the foregoing tumor rejection peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci USA* 92(13):5845–5849, 1995; Gilbert et al., *Nature Biotechnol.* 15(12):1280–1284, 1997; Thomson et al., *J. Immunol.* 157 (2):822–826, 1996; Tam et al., *J. Exp. Med.* 171(1):299–306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951–1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

As part of the immunization protocols, substances which potentiate the immune response may be administered with nucleic acid or peptide components of a cancer vaccine. Such immune response potentiating compound may be classified as either adjuvants or cytokines. Adjuvants may enhance the immunological response by providing a reservoir of antigen (extracellularly or within macrophages), activating macrophages and stimulating specific sets of lymphocytes. Adjuvants of many kinds are well known in the art; specific examples include MPL (SmithKline Beecham), a congener obtained after purification and acid hydrolysis of *Salmonella minnesota* Re 595 lipopolysaccharide, QS21 (SmithKline Beecham), a pure QA-21 saponin purified from *Quillja saponaria* extract, DQS21, described in PCT application WO96/33739 (SmithKline Beecham), vitamin E and various water-in-oil emulsions prepared from biodegradable oils such as squalene and/or tocopherol. Cytokines are also useful in vaccination protocols as a result of lymphocyte stimulatory properties. Many cytokines useful for such purposes will be known to one of ordinary skill in the art, including interleukin-12 (IL-12) which has been shown to enhance the protective effects of vaccines (*Science* 268: 1432–1434, 1995), GM-CSF and IL-18.

There are a number of additional immune response potentiating compounds that can be used in vaccination protocols. These include costimulatory molecules provided in either protein or nucleic acid form. Such costimulatory molecules include the B7-14 1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation .,and effector function. B7 also interacts with CTLA4 (CD 152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284–6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637–5648, 1995). Tumor cell transfection with B7 has been discussed in relation to in vitro CTL expansion for adoptive transfer immunotherapy by Wang et al. (*J. Immunother.* 19:1–8, 1996). Other delivery mechanisms for the B7 molecule would include nucleic acid (naked DNA) immunization (Kim et al., *Nature Biotechnol.* 15:7:641–646, 1997) and recombinant viruses such as adeno and pox (Wendtner et al., *Gene Ther.* 4:726–735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered.

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637–642, 1997; Fenton et al., *J. Immunother.*, 21:95–108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature* 393:474, 1998; Bennett et al., *Nature* 393:478, 1998; Schoenberger et al., *Nature* 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art. In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the MAGE-3 immunogen(s) employed. These desired responses can be monitored by routine methods or can be monitored according to diagnostic methods of the invention discussed herein.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 miligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

EXAMPLES

Figure 1:
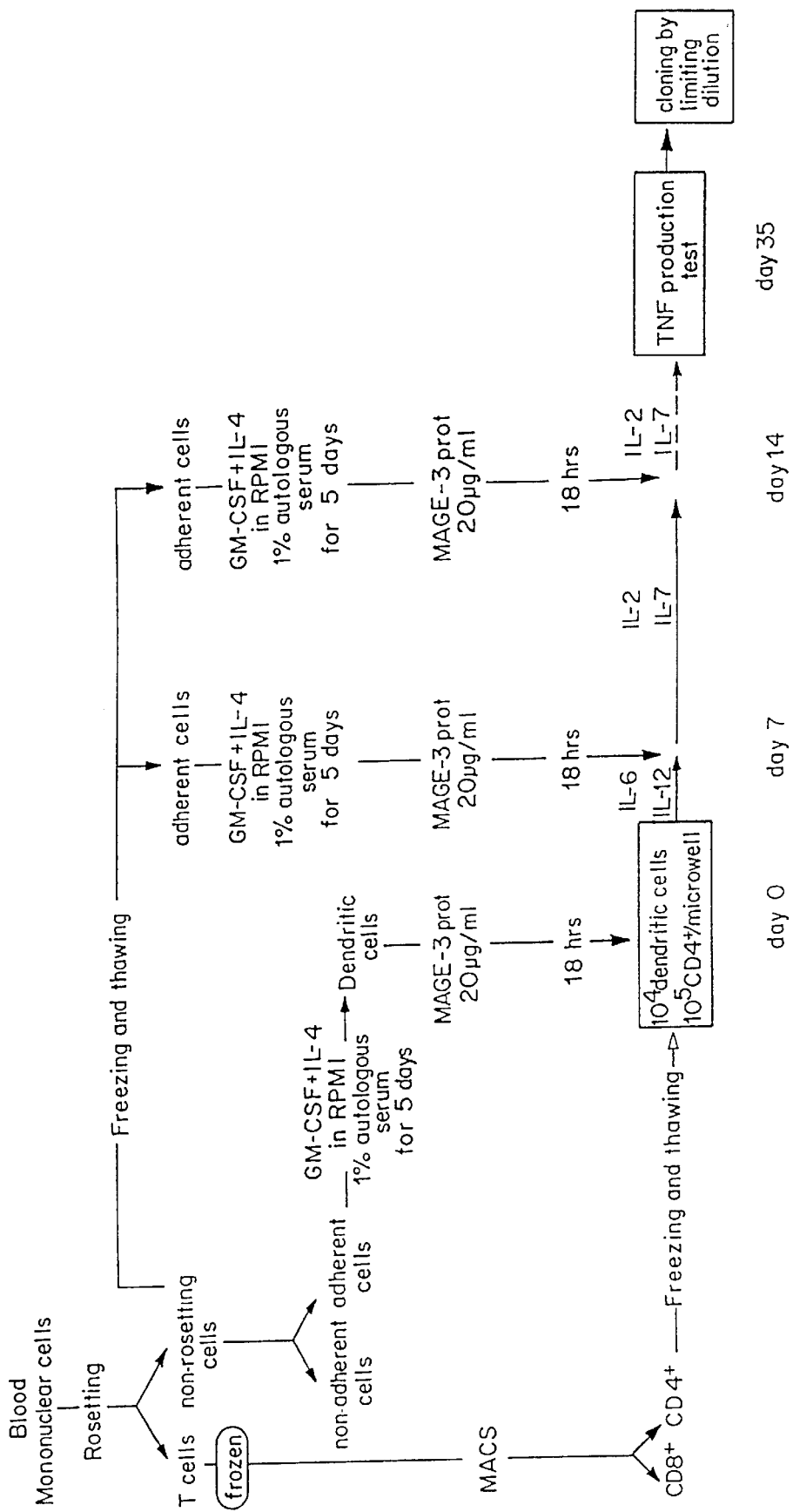
FIG. 1 is a schematic representation of the protocol used to obtain CD4 T cell lines specific for MAGE-3.

We have identified antigenic peptides encoded by gene MAGE-3 and presented to T cells in the context of HLA class II molecules. The strategy has consisted of loading dendritic cells of normal blood donors with a recombinant MAGE-3 protein and to use these antigen-presenting cells to induce in vitro the activation and proliferation of specific CD4 lymphocytes. The protocol is described below (A, B, C) and in FIG. 1.

A. Processing of Human Blood

Peripheral blood was obtained from the local blood bank (non cancer patients, e.g., hemochromatosis patients) as standard buffy coat preparations. Peripheral blood mononuclear cells (PBMC) were isolated by centrifugation on Lymphoprep (Nycomed Pharma, Oslo, Norway). In order to minimize contamination of PBMC by platelets, the preparation was first centrifuged for 20 min/1000 rpm at room temperature. After removal of the top 20–25 ml, containing most of the platelets, the tubes were centrifuged for 20 min/1,500 rpm at room temperature. PBMC were depleted of T cells by resetting with 2-aminoethylisothiouronium (Sigma) treated sheep erythrocytes. The lymphocyte-depleted PBMC were left to adhere for 2 hours at 37° C. in culture flasks (Falcon) at a density of $2\times10^6$ cells/ml in RPMI 1640 medium supplemented with L-asparagine (0.24 mM), L-arginine (0.55 mM), L-glutamine (1.5 mM) and 1% autologous serum (complete medium). Non-adherent cells were discarded and adherent cells were cultured in the presence of IL-4 (100 U/ml) and GM-CSF (100 ng/ml) in complete medium. Cultures were fed on day 2 and 4 by removing 5 ml of the medium and adding back fresh medium with IL-4 (100 U/ml) and GM-CSF (100 ng/ml). On day 5, the non-adherent cell population was used as a source of enriched dendritic cells.

Rosetted T cells were treated with $NH_4Cl$ (160 mM) to lyse the sheep erythrocytes, and washed. $CD4^+$ T lymphocytes were isolated from rosetted T cells by negative selection using an anti-CD8 monoclonal antibody coupled to magnetic microbeads (Miltenyi Biotech, Germany) by sorting through the MACS magnet as recommended by the manufacturer.

B. Cytokines

Human recombinant IL-2 was donated by Biogen (Geneva, Switzerland) and also was purchased from Chiron (Emeryville, Calif.). Human recombinant IL-4, IL-6 and IL-12 were obtained in our laboratory. Human recombinant IL-7 was purchased from Genzyme (Cambridge, Mass.). Human recombinant GM-CSF was donated by Sandoz (Sandoz Pharma, Basel, Switzerland) or purchased from Schering Plough (Brinny, Ireland). Human recombinant TNF-α was purchased from R & D Systems (Abingdon, UK).

C. Feeding with Protein or Cell Lysates and Mixed Lymphocyte-dendritic Cells Culture The recombinant His-MAGE-3 protein (MAGE-3 with a His tag) and LipoD-MAGE-3-His protein were produced by Smith Kline Corporation Pharmaceutical Company (Rixensart, Belgium) in *E. coli* and purified by standard chromatographic procedures. LipoD-MAGE-3-His contains one third of the lipidic form of the *Haemophilus influenzae* protein at its N-terminal residue and a polyhistidine marker at its C-terminal residue.

Autologous dendritic cells ($5\times10^5$) were incubated at 37° C., 5% $CO_2$, for 18–20 hours in RPMI medium supplemented with 1% autologous serum, IL-4 (100 U/ml), GM-CSF (100 ng/ml) and TNF-α (1 ng/ml) in the presence of the recombinant His-MAGE-3 protein (20 μg/ml). His-MAGE-3 protein-pulsed dendritic cells were washed and added at $10^4$ per round-bottomed microwell to $10^5$ $CD4^+$ T lymphocytes in 200 μl Iscove's medium supplemented with 10% human serum, L-asparagine (0.24 mM), L-arginine (0.55 mM), L-glutamine (1.5 mM) in the presence of IL-6 (1000 U/ml) and IL-12 (10 ng/ml). The $CD4^+$ lymphocytes were weekly restimulated with autologous dendritic cells freshly pulsed with the His-MAGE-3 protein and were grown in complete Iscove medium supplemented with IL-2 (10 U/ml) and IL-7 (5 ng/ml). Due to the short supply of dendritic cells for melanoma patient 7002, only $6\times10^3$ dendritic cells were used, instead of $10^4$, and restimulation was performed on days 10, 20 and 30.

Dendritic cells were used for the presentation of lysates of 293-EBNA cells expressing MAGE-3. The MAGE-3 sequence cloned into the expression vector pCEP-4 was transiently transfected into the 293-EBNA cell line by LipofectAMINE® (GIBCO/BRL). Briefly, $5\times10^4$ 293-EBNA cells per flat-bottomed microwell were transfected with 6,18, 53 or 160 ng of plasmid pCEP4-MAGE-3 and 1 μl of LipofectAMINE® in OptiMEM medium (GIBCO/BRL). After 24 h, transfected 293-EBNA cells were lysed in 50 μl of complete RPMI medium by three cycles of rapid freezing-thawing. Monocyte-derived dendritic cells expressing the HLA-DR13 molecules were then added ($1.5\times10^4$ cells per well) on the lysates of transfected 293-EBNA cells and maintained at 37° C. for 24 hr. Dendritic cells were then washed before adding the $CD4^+$ clone. Supernatants were harvested after 20 h and assessed for IFN-γ secretion.

Example 1

Obtention of CD4 T Cell Lines and Clones Specific for MAGE-3

The microcultures that contained proliferating $CD4^+$ T cells were assessed around 35 days after the start of the culture for their capacity to produce TNF and/or IFN-γ when stimulated with autologous EBV-B cells pulsed with the His-MAGE-3 protein. Autologous EBV-B cells (500,000/ml) were incubated for 18–20 hours at 37° C. in the presence of 20 μg/ml of His-MAGE-3 protein, or Ovalbumin (Sigma) as a negative control. EBV-B cells referred to herein are B cells which were immortalized with Epstein Barr virus. The EBV-B cells were prepared according to art-standard procedures. Protein-pulsed EBV-B cells were washed and added at 5,000 per round-bottomed microwell to 2,500 $CD4^+$ T lymphocytes in 150 μl of complete Iscove's medium supplemented with L-glutamine, L-arginine, L-asparagine, 10% human serum and IL-2 (25 U/ml). After 18–20 hours, supernatants were harvested and assessed for TNF content by testing the cytotoxic effect of the supernatants on TNF-sensitive WEHI 164 clone 13 cells as previously described (Espevik and Nissen-Meyer, *J. Immunol. Methods* 95:99–105, 1986) in a MTT colorimetric assay as previously described (Hansen et al.,*J. Immunol. Methods* 119:203–210, 1989; Traversari et al., *Immunogenetics* 35:145–152, 1992). IFN-γ production was measured using an ELISA assay developed in our laboratory (see below) with reagents from Medgenix Diagnostics-Biosource (Fleurus, Belgium). Inhibition with mAbs W6/32 (anti-HLA class I) or 2B6 (anti-HLA-DR) was performed by addition of a 1/20 dilution of ascites during the experiment. Cytokine secretion in response to autologous EBV-B cells pulsed with MAGE-3 was considered significant if it was at least twofold above the background response of T cells to EBV-B cells pulsed with ovalbumin, and if it exceeded 500 pg of INF-γ or 50 pg/ml of TNF per ml.

Figure 2:
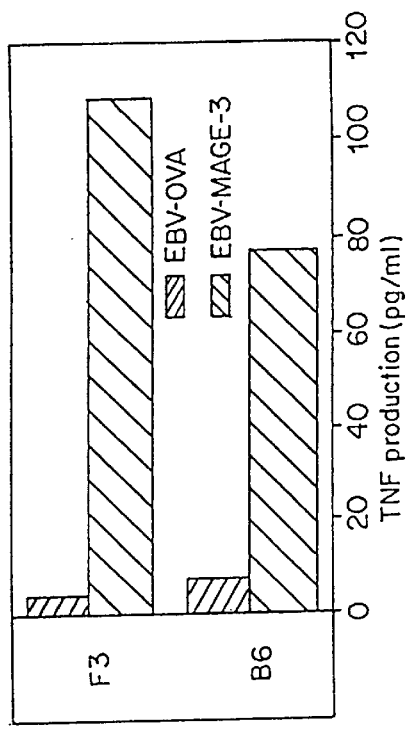
FIG. 2 is a graph showing CD4+ T cell lines B6 and F3 recognized autologous EBV-B cells which have processed the recombinant His-MAGE-3 protein.

The CD4+ T cell lines producing TNF specifically (FIG. 2), i.e. those which recognized the MAGE-3 protein, were cloned by limiting dilution, using the autologous EBV-B cell line pulsed with exogenous His-MAGE-3 protein or LipoD-MAGE-3-His protein as stimulating cells and allogeneic EBV-B cells (LG2-EBV) as feeder cells. CD4+ T cell clones were grown in complete Iscove's medium supplemented with IL-2 (50 U/ml), IL-7 (5 ng/ml) and 0.5 µg/ml purified PHA (Murex Diagnostics, Dartford, GB). The clones were supplemented with fresh culture medium once a week and passaged with feeder cells (1.5×10⁶ allogeneic PBL plus 5×10LG2-EBV transformed cells per 24 well plate) at 1–2 weeks intervals. In some instances, clones were restimulated using the autologous EBV-B cell line retrotransduced with Ii.MAGE-3, using 2×10⁵ stimulating cells plus 10⁶ LG2 EBV-B transformed cells per 24 wells plate.

Figure 3:
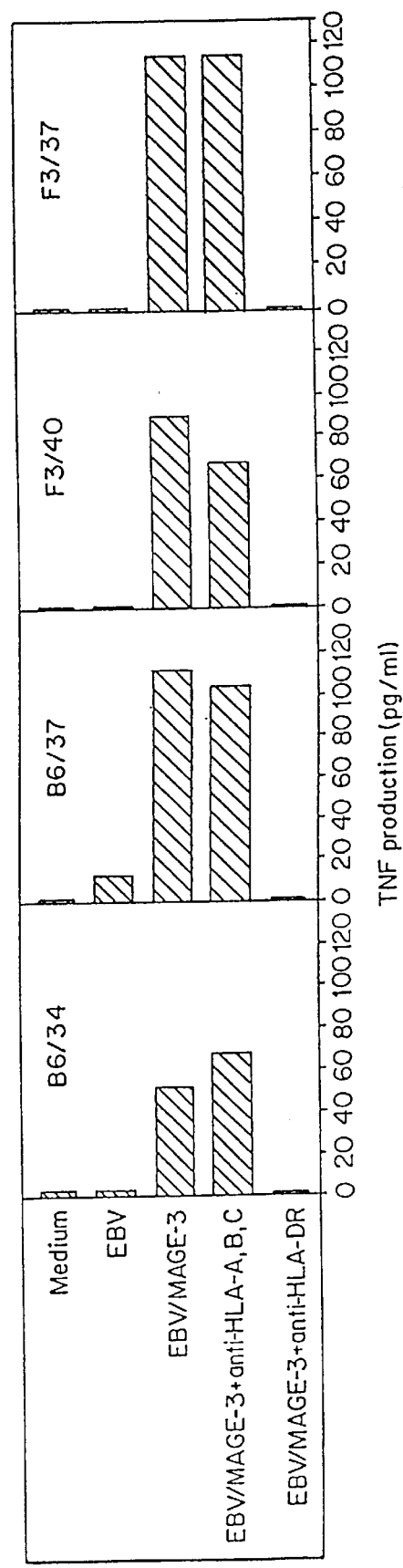
FIG. 3 is a graph showing that the recognition by CD4+ T cell clones of autologous EBV-B cells pulsed with exogenous His-MAGE-3 protein is inhibited by an anti-HLA DR monoclonal antibody.

Established CD4+ T cell clones were then tested for TNF and/or INF-γ secretion upon stimulation with autologous EBV-B cells pulsed with the exogenous His-MAGE-3 or LipoD-MAGE-3-His protein, as described above. Briefly, the assay was a standard ELISA in which INF-γ antibodies were coated onto the wells of plastic microtiter plates prior to incubation with cell supernatants to determine the amount of INF-γ produced. Any INF-γ ELISA assay could be used to measure INF-γ produced. Several MAGE-3 specific clones were obtained from the B6 line (FIG. 3).

The MAGE-3 epitope is presented to the CD4 clones by HLA-DR molecules (FIG. 3): MAGE-3-pulsed EBV-B cells were cocultured for 24 hours at 37° C. under 8% $CO_2$ with MAGE-3 specific CD4+ clones, in the continuous presence of preservative-free monoclonal antibodies used at a 1/20 dilution. Monoclonal antibody 2B6 (against HLA-DR) abolished the recognition whereas the recognition is unchanged in the presence of monoclonal antibody W6/32 (against HLA-A, B, C).

Example 2

Identification of the MAGE-3 HLA-DR Restricted Peptide

Figure 4:
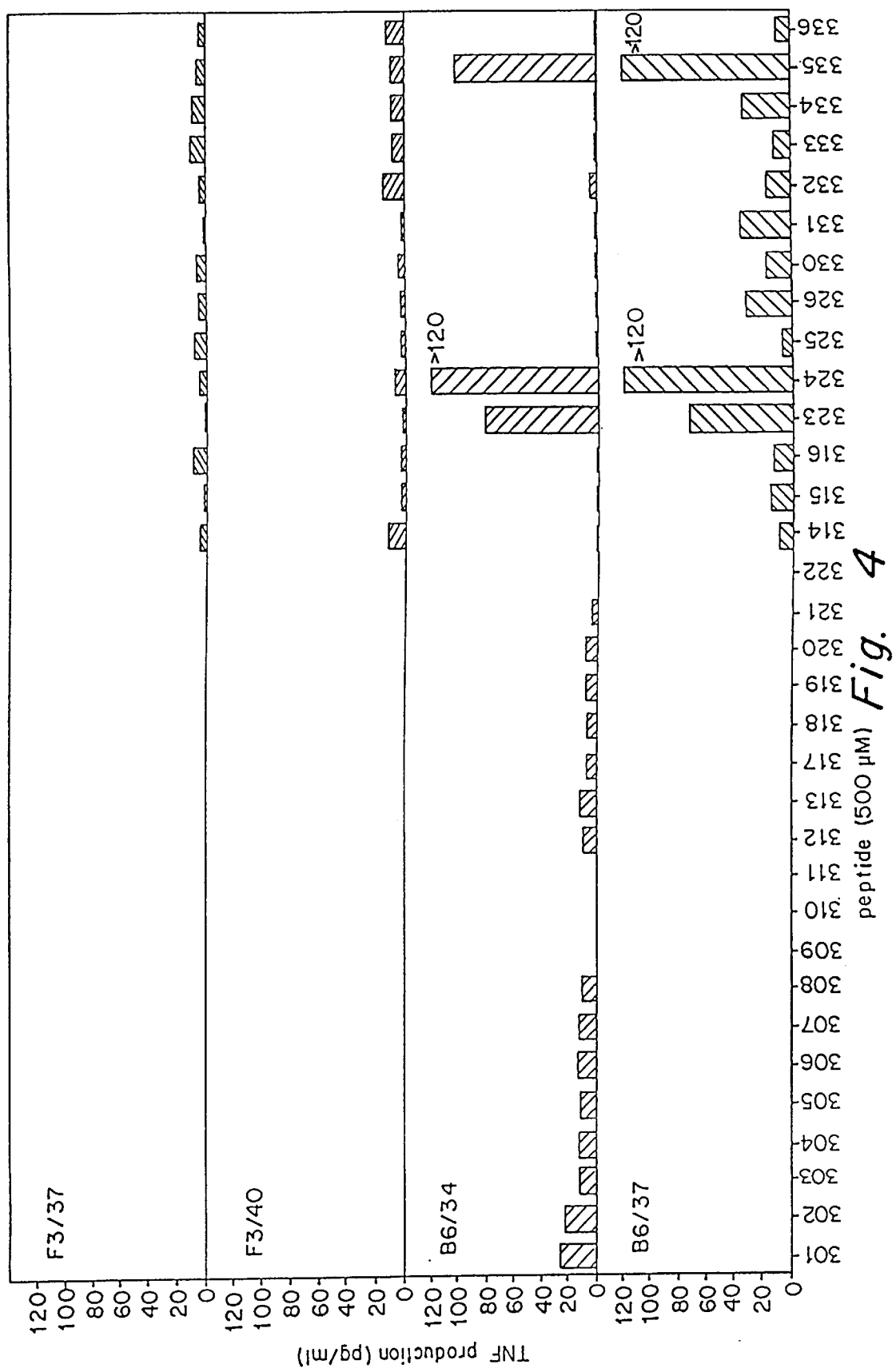
FIG. 4 is a graph detailing the screening of MAGE-3 peptides for recognition by CD4+ clones 436/B6.34 (B6/34), 436/B6.37 (B6/37), F3/37 and F3/40.
Figure 5:
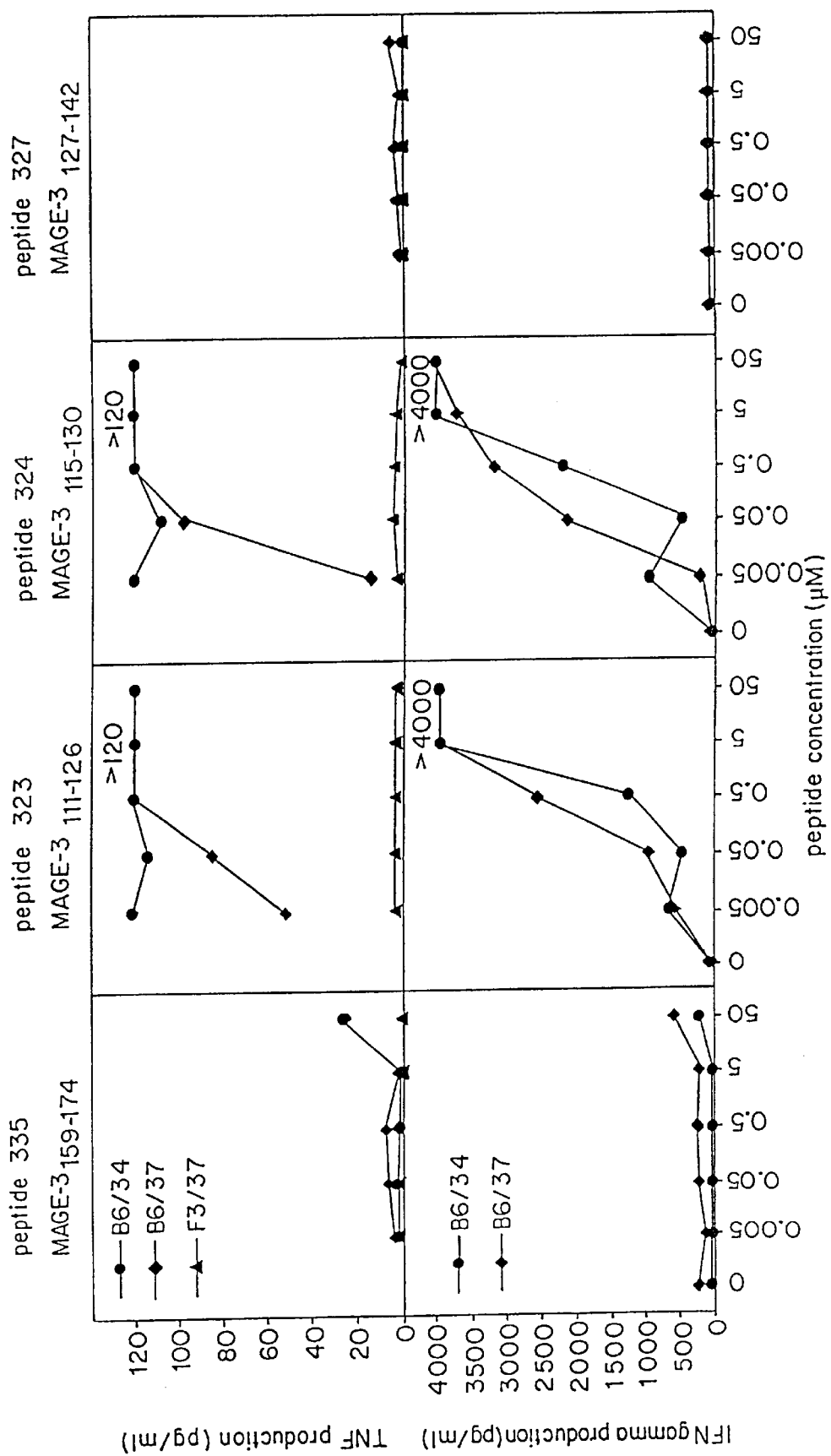
FIG. 5 is a graph depicting stimulation of TNF and IFN-γ production by CD4+ clones 436/B6.34 (B6/34) and 436/

In order to identify the MAGE-3 peptides recognized by these CD4+ clones, 16 amino acid peptides, corresponding to parts of the MAGE-3 protein sequence were synthesized, loaded on the autologous EBV-B cells and tested for recognition (FIGS. 4 and 5). Peptides were synthesized using F-moc for transient $NH_2$-terminal protection and were characterized using mass spectrometry. All peptides were >80% pure as indicated by analytical HPLC. Lyophilized synthetic peptides were dissolved in DMSO (Merck) and used at a final concentration of 500 µM, 50 µM or 5 µg/ml. EBV-B cells (5,000 per round-bottomed microwell) were incubated 2 hours at 37° C., 8% $CO_2$ in the presence of the different peptides, the indicated concentrations representing the peptide concentration during the incubation step. CD4+ clones were then added at 2,500 cells per well. Assay medium was Iscove's medium supplemented with L-glutamine, L-arginine, L-asparagine, 10% human serum and IL-2 (25 U/ml). After 18–20 hours, supernatants were harvested and assessed for TNF-α and/or INF-γ secretion. INF-γ production was measured using an ELISA test (20–4000 pg/ml) developed in the laboratory with reagents from Medgenix Diagnostics-Biosource (Fleurus, Belgium).

In one set of experiments, the peptides were screened at a non-physiologic concentration of 500 µM. Non-physiologic concentrations of peptide may lead to non-specific activation of T cells clones. Indeed, when used at 500 µM, peptide MAGE-$3_{159-174}$ (FIG. 4-peptide 335; SEQ ID NO:6) induced activation of clones 436/B6.34 (B6/34) and 436/B6.37 (B6/37), but this peptide was not effective in activating these clones when used at 50 µM (FIG. 5). On the contrary, the peptides RKVAELVHFLLLKYRA (MAGE-$3_{115-126}$-FIG. 4-peptide 323; SEQ ID NO:3) and ELVHFLLLKYRAREPV (MAGE-$3_{115-130}$-FIG. 4-peptide 324; SEQ ID NO:4) stimulated specifically TNF-α and INF-γ production by clones B6/34 and B6/37 when used at more physiologic concentrations or preferably lower concentrations. These two peptides were also able to induce the proliferation of the B6 clones (FIG. 6).

As shown in FIGS. 3–6, clones F3/40 and F3/37 did not recognize MAGE-3 peptides, did recognize cells presenting MAGE-3. Thus it is believed that these two clones recognize a cellular component rather than MAGE-3.

Example 3

Determination of the HLA Restriction Element Utilized by MAGE-3 Specific CD4+ Clone B6/37

Cytokine secretion by these CD4+ clones in response to autologous EBV-B cell pulsed with the His-MAGE-3 protein is restricted to HLA-DR. To further define the HLA-restriction element utilized by clone B6/37, additional EBV-B cell lines were used for peptide presentation as described above (FIG. 7). HLA serotyping of AUMA-EBV (LB 1622-EBV), LB 1555-EBV, GERL-EBV (MZ2-EBV) revealed that class II molecules shared by all three cell types were limited to HLA-DRB1/1302. Moreover, ADET-EBV: (LB1118-EBV) was found to present effectively the MAGE-$3_{115-130}$ peptide and the HLA serotyping of these cells was found to be HLA-DRB1/1301. Screening of several other EBV-B cell lines as described above for their ability to stimulate clone B6/37 when pulsed with peptide MAGE-$3_{111-126}$ and MAGE-$3_{115-130}$ was performed to confirm that both HLA-DRB1/1301 and HLA-DRB1/1302 can present these peptides (Table II).

TABLE II

| EBV-B cell line | IFN-γ production (pg/ml) by clone B6/37 stimulated by peptide | |
|---|---|---|
| | MAGE-$3_{111-126}$ | MAGE-$3_{115-130}$ |
| DR13 positive | | |
| LB1118 | 3761 | 3909 |
| LB1555 | >4000 | >4000 |
| LB1622 | 1731 | 1349 |
| MZ2 | 3429 | 3096 |
| OMW | >4000 | >4000 |
| DR13 negative | | |
| BM16 | 99 | 120 |
| BOB | 128 | 101 |
| BOLETH | 77 | 67 |
| LKT3 | 6 | 27 |
| OLGA | 117 | 68 |
| RML | 134 | 129 |
| RSH | 140 | 87 |
| TAB089 | 52 | 55 |
| TISI | 119 | 179 |
| VAF | 62 | 178 |
| VET | 105 | 135 |

Screening of other EBV-B cell lines as described above for their ability to stimulate clones B6/34 and/or B6/37 when pulsed with peptide peptide MAGE-$3_{111-126}$ and/or MAGE-$3_{115-130}$ is performed to define other HLA-DRB1/13 presenting. molecules.

Example 4

Determination of Minimal Peptides Still Able to Stimulate B6/37 Clone

Unlike HLA-class I-restricted peptides, class II-restricted peptides vary considerably in length and can tolerate extensions at both the amino and carboxy termini. It was demonstrated that both peptides MAGE-$3_{111-126}$ and MAGE-$3_{115-130}$ stimulated specifically clones B6/34 and B6/37, whereas peptides MAGE-$3_{107-122}$ and MAGE-$3_{119-134}$ were unable to activate these clones. Therefore, the MAGE-$3_{115-126}$ peptide (ELVHFLLLKYRA; SEQ ID NO:9) may be the minimal 12 amino-acids motif necessary for activation of B6/34 and B6/37 clones. As expected, peptide MAGE-$3_{115-126}$ induced significant production of INF-γ by clone B6/37 (FIG. 8). Shortened peptides having deletions of one residue or more also were prepared. Several of the shortened peptides, e.g. MAGE-$3_{116-126}$ (SEQ ID NO:10) and MAGE-$3_{117-126}$ (SEQ ID NO:11), also induced INF-γ production by clone B6/37 (FIG. 8), albeit reduced amounts of INF-γ. MAGE-$3_{118-126}$ (SEQ ID NO:12) did not induce the production of significant amounts of INF-γ.

Example 5

Presentation of Exogenous MAGE-3 by Dendritic Cells

Clone 37 was obtained with autologous dendritic cells heavily loaded with MAGE-3 protein. To determine the ability of dendritic cells that capture a quantity of MAGE-3 protein released by a few MAGE-$3^+$ cells to stimulate CD4$^+$ T cells, HLA-DR13 dendritic cells were incubated for 24 h with decreasing concentrations of MAGE-3 as depicted in (FIG. 9A). Stimulation of clone 37 was tested by washing the cells, distributing the cells in round-bottomed microwells, and adding 2500 clone 37 cells. INF-γ secretion was measured by ELISA after 20 h of coculture. Experiments were performed in triplicate. Half maximum production of INF-γ was obtained when $10^4$ dendritic cells in a volume of 100 μl were pre-incubated with 30 ng of MAGE-3, the quantity of MAGE-3 present in around $2 \times 10^4$ MZ2-MEL.43 tumor cells. This result suggests that dendritic cells which endocytose debris of very few tumor cells expressing MAGE-3 are able to stimulate clone 37.

Another assay was performed to test the ability of dendritic cells to process the debris of MAGE-$3^+$ cells: MAGE-3 was transiently transfected into 293-EBNA cells, which were subsequently lysed. HLA-DR13 dendritic cells were first incubated for 24 h with lysates and then used to stimulate clone 37. In three separate experiments, clone 37 was stimulated by dendritic cells incubated with lysates of 293-EBNA cells transfected with pCEP4-MAGE-3 as judged by INF-γ release (FIG. 9B). 293-EBNA cells($5 \times 10^5$ cells per well) were tranfected with different doses of pCEP4-MAGE-3 mixed with lipofectAMIN®, and lysed 24 h after transfection. HLA-DR13 dendritic cells were cultured 24 h with 293-EBNA lysate (the equivalent of 5 cells per dendritic cell). Dendritic cells were then washed, distributed in round-bottomed microwells, and 2500 cells of clone 37 were added. INF-γ secretion was measured by ELISA after 20 h of coculture. The experiment was performed in triplicate.

Example 6

Preparation and Use of MAGE-3 Fusion Proteins

The MAGE-3 protein was expressed in an EBV B cell line MZ2 EBV (HLA A1 DR13) as a fusion protein with a truncated invariant chain (Ii) or with the lysosome-associated membrane protein (LAMP-1) to target the presentation of MAGE-3 derived peptides in HLA class II molecules (see schematic drawing in FIG. 14). Transduction of Ii MAGE-3 yielded peptide presentation in HLA class II, as measured by the recognition by the CD4 T cell clone LB 1555 CD4 436/B6.37, which reacts with the MAGE-3.DR13 epitope. In addition, expression of Ii MAGE-3 in EBV B cells resulted in peptide presentation in HLA class I, which was determined by the activation of the MAGE-3.A1 specific CTL clone LB 705 434/1. In contrast, expression of the MAGE-3-LAMP-1 fusion protein only marginally enhanced the presentation of MAGE-3 peptide in HLA molecules. Connecting the Ii to MAGE-3 therefore can be used as a vaccine to induce presentation of MAGE-3-derived peptides in both HLA class I and class II.

Plasmids and Cloning of Fusion Constructs

MAGE-3: The MAGE-3 cDNA and polypeptide are set forth as SEQ ID NO:1 and SEQ ID NO:2, respectively.

Human invariant chain: The plasmid named IipSV51L containing the human invariant chain encoding cDNA was kindly provided by Dr. J. Pieters (Basel Institute for Immunology, Basel, Switzerland; *J. Cell Science* 106:831–846, 1993).

LAMP1: The plasmid pCMV-sig E7-LAMP 1 was kindly provided by Dr. T. Wu (Johns Hopkins University, Baltimore, Md., USA; *Proc. Natl. Acad. SCi. USA* 92:11671–11675, 1995).

pMFG: The plasmid pMFG was kindly provided by Dr. O. Danos (Somatix Therapy Corporation, Alameda, Calif., USA).

Construction of pMFG-MAGE-3:

The MAGE-3 cDNA was transferred to the pMFG vector after the introduction of the appropriate restriction enzyme recognition sites at the 5' and 3' end of the coding sequence. A NcoI site was introduced at the 5' site and a BglII site at the 3' end by PCR using the primers: NcoI-sense: 5'-TTTCCATGGCTCTTGAGCAGAGGAGTCAGC-3' (SEQ ID NO:14) and BglII-antisense: 5'-CCCAGATCTTCACTCTTCCCCCTCTCTC-3' (SEQ ID NO:15) [the recognition sites for NcoI and BglII are in italics]. The PCR product was cloned into a pCR2.1 and sequenced according to standard methods. The NcoI-BglII amplification product was cloned into pMFG opened with the enzymes NcoI and BamHI.

Construction of pMFG-Ii.MAGE-3

The cDNA encoding the amino terminal end (i.e. the cytoplasmic tail and the transmembrane region) of the human invariant chain polypeptide (hu-Ii; residues 1–80) was amplified by PCR using IipSV51L as template. The following primers were used: hu-Ii sense: 5'-TTTCCATGGATGACCAGCGCGAC-3' (SEQ ID NO:16); and hu-Ii antisense: 5'-TTTGGATCCGGAAGCTTCATGCGCAGGTTC-3' (SEQ ID NO:17) [the recognition sites for NcoI and BamHI are in italic]. The PCR product was cloned into pCR2.1 and sequenced according to standard methods. The NcoI-BamHI amplification product was cloned into pMFG, opened with the enzymes NcoI and BamHI resulting in pMFG-Ii.

A BglII recognition site, replacing the ATG codon and in frame with the BamHI site at the 3' end of the truncated Ii-cDNA, was introduced at the 5' end of the MAGE-3 cDNA by PCR using the primers: BglII-sense: 5' TTTAGATCTTGAGCAGAGGAGTCAGC-3' (SEQ ID NO:18) and BglII-antisense (SEQ ID NO:15) [the recognition sites for BglII are in italic]. The PCR product (BglII.MAGE-3.BglII) was cloned into pCR2.1 and sequenced according to standard methods.

The recombinant plasmid pMFG-Ii was reopened with BamHI and the BglII.MAGE-3.BglII amplification product was ligated to the compatible ends. Recombinant plasmids containing the MAGE-3 cDNA in frame and in the right orientation were identified by restriction fragment analysis.

Construction of pMFG-Sig.MAGE-3.LAMP-1

The cDNAs encoding the signal peptide of the LAMP-1 protein and the transmembrane domain and cytoplasmic tail of LAMP-1 were amplified by PCR using pCMV-sig E7-LAMP1 as template. The primer set for the signal peptide of LAMP-1 was: Sig sense: 5'-CCCCCATGGCGGCCCCCGGC-3' (SEQ ID NO:19) and Sig antisense: 5'-GGGGGATCCTCAAAGAGTGCTGA-3' (SEQ ID NO:20) [the recognition sites for NcoI and BamHI are in italic]. The BamHI site at the 3' end of this cDNA is in frame with the BglII site at the 5' end of the BglII.MAGE-3.BglII fragment. The amplification product was cloned into pMFG to prepare pMFG-Sig.

The primer set for the amplification of the LAMP1 transmembrane domain and cytoplasmic tail was: LAMP-1 sense: 5'-GGGGGATCCTAACAACATGTTGATCCCC-3' (SEQ ID NO:21) and LAMP-1 antisense: 5'-GGGAGATCTCTAGATGGTCTGGGTCTGA TAGCCGGC-3' (SEQ ID NO:22) [the recognition sites for BamHI and BglII are in italic]. The amplification product was sequenced according to standard methods and cloned into pMFG-Sig, resulting in plasmid pMFG-Sig.LAMP-1 with an unique BamHI site at the junction of the signal peptide and the transmembrane sequence. To generate the plasmid pMFG-Sig.MAGE-3.LAMP-1, a BglII-BamHI fragment isolated from the BglII.MAGE-3.BglII cDNA was cloned into pMFG-Sig.LAMP-1 opened with BamHI. This cloning step deleted the 3' end of MAGE-3 encoding amino acids 240–314.

Cell Lines Media and Reagents

The PhoenixAMPHO cell line (kindly provided by Dr. Nolan, Stanford University School of Medicine, Calif., USA) is a high titer amphotropic retrovirus producing cell line that has been generated by stable transfection of 293T cells with a Moloney GagPol-IRES-Lyt 2 construct with an RSV promoter and a pPGK hygro selectable marker. These cells were then stably transfected with the Moloney amphotropic envelope gene driven by a CMV promoter and co-selected with the diphtheria toxin resistance gene (pHED-7). This producer cell line is helper virus free.

PhoenixAMPHO cells were cultured and passaged in 175 cm² flasks in DMEM (Life Technologies, Ghent, Belgium) supplemented with 10% heat inactivated FCS, 2 mM L-glutamine, 100 U/ml penicillin and 100 µg/ml streptomycin.

The MZ2-EBV B cell line was generated from B cells of melanoma patient MZ2 (HLA A1 A29 DR0101 DR1302) by infection with EBV. Likewise, the LG2-EBV B cell line was generated from non-cancer patient LG2 (HLA A24 A32 DR7 DR14). MZ2-MEL.43 is a melanoma cell line from patient MZ2. The EBV transformed B cell lines and MZ2-MEL.43 were cultured in Iscove's modified Dulbecco's (ID) medium supplemented with 10% foetal calf serum (FCS), 0.24 mM L-asparagine, 0.55 mM L-arginine and 1.5 mM L-glutamine (AAG).

The cytotoxic T cell clone LB 705 CTL 434/1 is directed against the MAGE-3.A1 epitope and was generated in a primary culture of CD8⁺ T cells from non-cancer patient LB705 (HLA A1 A2) and irradiated autologous PBL (peripheral blood lymphocytes) pulsed with the MAGE-3.A1 peptide. The CD4 T cell clone LB 1555 CD4 436/B6.37 recognized the MAGE-3.DR13 epitope and was identified by a primary culture of T cells of patient LB 1555 DESA (HLA DR3 DR1302) and autologous monocyte-derived dendritic cells preincubated with purified MAGE-3 protein. The T cell clones were cultured in ID supplemented with 10% heat-inactivated human serum (HS), AAG and 50 U/ml recombinant human IL-2 (rh IL-2) in the presence of irradiated feeder cells (LG2-EBV, pooled human PBL) and specific stimulating cells (MZ2-MEL-43 for CTL 434/1 or DESA-EBV preincubated with the MAGE-3 protein for the CD4 T cell clone 436/B6.37).

Generation of High Titer MAGE 3 Encoding Recombinant Retrovirus

The MAGE-3 encoding retroviral vector plasmids, MFG-MAGE-3, MFG-Ii.MAGE-3, MFG-Sig.MAGE-3.LAMP and MFG-EGFP (encoding enhanced green fluorescent protein reporter), were introduced into the PhoenixAMPHO packaging cells by transfection. The MFG retroviral vector is derived from Moloney murine leukemia virus and is lacking in a drug resistance marker nor does it express any other potential antigenic protein except for the inserted cDNA (Riviere, $Proc.\ Natl\ Acad.\ Sci.\ USA$ 92:6733–6737, 1995). The transfection procedure is a modification of the calcium phosphate-mediated transfection protocol of Graham and van der Eb ($Virology$ 54:536–539).

Twenty four hours prior to transfection, $10.8 \times 10^6$ PhoenixAMPHO cells were plated in 14 ml cell growth medium in a 75 cm² tissue culture flask (Falcon). After adding the cells, the flask was gently shaken forward and backward to distribute cells evenly about the flask bottom. The cells were incubated at 37° C. and 5% $CO_2$. At the time of transfection, when the cells should have reached a confluence of 70–80%, the medium was removed and was replaced by 14 ml fresh PhoenixAMPHO cell growth medium containing 25 mM chloroquine (Sigma Chemical Co., St. Louis, Mo., USA). A transfection cocktail was prepared in a 50 ml tube by adding 40 µg retroviral vector plasmid DNA to water and diluting to 1575 µl final volume. To this DNA solution 225 µl of 2 M $CaCl_2$ (Sigma) was added. Then, 1800 µl of 2×HeBS (50 mM HEPES, 10 mM KCl, 12 mM dextrose, 280 mM NaCl and 1.5 mM $Na_2HPO_4$ dissolved in distilled water, filtered through 0.2µ filter and stored at −20° C.) was added dropwise to the DNA/$CaCl_2$ solution by vigorously bubbling for 15 seconds with an automatic pipette. The DNA/$CaCl_2$/HeBS mix was added immediately and dropwise onto the cells and the flask was gently swirled to ensure uniform mixing of DNA/$CaPO_4$ particles. The cells were incubated at 37° C./5% $CO_2$ for 7 to 9 hours and the chloroquine containing medium was changed for fresh PhoenixAMPHO cell growth medium. Approximately 24 hours prior to the harvest of the retroviral supernatant, the PhoenixAMPHO medium was removed and gently replaced by 9 ml of EBV cell growth medium (Iscove's) containing only 2.5% FCS. The retroviral supernatant was harvested 48 hours following transfection by removing the medium from the cells and filtering through a 0.45µ filter to remove cell debris. After harvest and filtration, the virus containing medium was kept on ice, aliquoted in appropriate volumes in 15 ml polypropylene tubes and stored at −80° C. The MFG-EGFP transfected PhoenixAMPHO cells were assayed for transfection efficiency by FACS analysis.

Retroviral Transduction of EBV Cell Lines

The EBV transformed cells were infected by resuspending the cells in an infection cocktail and centrifugation. Target cells were resuspended in 60 mm tissue culture plates (Falcon) at a density of $1.0 \times 10^6$ cells in 4 ml infection cocktail. The plates were centrifuged for 2 hours at 32° C. and 1200 ref in an IEC centrifuge, rotor type 228. For each plate to be transduced, 4 ml of injection cocktail was prepared by diluting the viral supernatant 1:2 in EBV cell growth medium and adding protamine sulfate to a final concentration of 6 $\mu$g/ml. Centrifugation was followed by another 2 hours of incubation in a humidified incubator at 37° C. and cells were transferred to 4 ml of target cell growth medium. This transduction cycle was carried out immediately after plating the cells and was repeated at 24 and 48 hours. The infected EBV cells were assayed for EGFP reporter gene expression by FACS analysis 24 to 48 hours following the third infection cycle.

Interferon-$\gamma$ Production Assay.

5000 T cells of LB705 CTL 434/1 or 3000 T cells of clone LB1555 CD4 436/B6.37 were washed and cultured overnight in the presence of 5000 retrovirally transduced EBV B cells of MZ2-EBV, or LG2-EBV B cells, in 100 $\mu$l ID medium containing 10% HS, AAG and 50 U/ml rh IL-2 in a round-bottom 96 wells plate. All cocultures were performed in triplicate. 50 $\mu$l culture supernatant was assayed for the presence of INF-$\gamma$ by ELISA (INF-$\gamma$ ELISA, Biosource). Briefly, ELISA plates precoated with anti-human INF-$\gamma$ Ab were washed and incubated with 50 $\mu$l culture supernatant and 50 $\mu$l biotinylated anti-human INF-$\gamma$ Ab (1:1250 in ID, 10% HS, AAG) for 2 h at room temperature (RT). After three washings the plates were incubated with 50 $\mu$l per well horseradish peroxidase conjugated streptavidin (1:3000 in PBS/0.5% BSA) for 30 min at RT, which was detected by TMB substrate, and $H_2SO_4$ to stop the reaction. The optical density was read at 450 nm. Samples containing 4000 pg/ml INF-$\gamma$ and 1:2 dilutions were used as standards.

Cytotoxicity Assay.

$1 \times 10^6$ EBV B cells were labeled with 25 $\mu$Ci $Na_2^{51}CrO_4$ for 60–90 min at 37° C. The cells were washed and resuspended at $1 \times 10^4$/ml. In control assays, MAGE-3.A1 peptide was added to the cell suspension at a concentration of 1 $\mu$M. LB705 CTL 434/1 T cells were cultured with 1000 labeled target cells per well in V shaped 96 well plates at 37° C. at effector to target cell ratios of 30 to 1 and ten-fold dilutions. After 4 h, the chromium release (ER) was measured in an aliquot of 100 $\mu$l supernatant. Target cells incubated in medium only or in 1% Triton were taken as minimal (SR) and maximal (MR) $^{51}$Cr release, respectively. The percentage experimental $^{51}$Cr release in the samples was calculated as: (ER-SR/MR-SR)$\times$100%.

Recognition of Transduced EBV B Cell Lines by T Cell Clone LB1555 CD4 436/B6.37.

MZ2 EBV were transduced with MFG Ii MAGE-3 (MZ2 EBV-Ii MAGE-3), MFG SigMAGE-3 LAMP (MZ2 EBV-SigMAGE-3 LAMP), MFG MAGE-3 (MZ2 EBV-MAGE-3) or with MFG EGFP (MZ2 EBV-EGFP). Transduced cells were cultured overnight in the presence of the CD4$^+$ T cell clone LB 1555 CD4 436/B6.37, which reacts with the MAGE-3.DR13 epitope. The T cell clone recognized MZ2-EBV-Ii MAGE-3, as determined by the release of INF-$\gamma$ in culture supernatant measured by ELISA (FIG. 10). In contrast, M2 EBV-SigMAGE-3 LAMP only induced a weak production of INF-$\gamma$. The control transfectants, MZ2 EBV-MAGE-3 and MZ2 EBV-EGFP, and LG2 EBV (not shown) were not recognized by the CD4 T cells. These results show that the Ii-MAGE-3 fusion protein is processed for presentation by HLA class II, whereas the MAGE-3 protein alone does not reach the HLA class II antigen presentation pathway.

Recognition of Transduced EBV B Cell Lines by LB 705 CTL 434/1.

Both MZ2 EBV-Ii MAGE-3 and MZ2 EBV-SigMAGE-3 LAMP were recognized to the same extent by the MAGE-3.A1 specific CTL clone LB 705 CTL 434/1 after overnight coculture (FIG. 11). INF-$\gamma$ release in the culture supernatant was measured by ELISA. MZ2 EBV-Ii MAGE-3 elicited a high INF-$\gamma$ production by the CTL clone, indicating that expression of the MAGE-3 protein fused to the Ii can still lead to processing in the HLA class I pathway.

The lysis by LB705 CTL 434/1 of MZ2-EBV retrovirally transduced with MAGE-3, Ii MAGE-3, SigMAGE-3 LAMP or GFP was tested in a 4 h $^{51}$Cr release assay at various effector to target cell (E/T) ratios. In parallel, MAGE-3.A1 peptide was added as a positive control for T cell activation. MZ2 EBV-Ii MAGE-3 and MZ2 EBV-SigMAGE-3 LAMP were both lysed by the LB705 CTL 434/1, similar to MZ2 EBV-MAGE-3. The percentage of lysis was equal to the target cell lysis in the presence of the MAGE-3.A1 peptide (FIG. 12).

Presentation of MAGE-3 Derived Peptide in HLA Class II by MZ2-MEL.43.

Figure 13A:
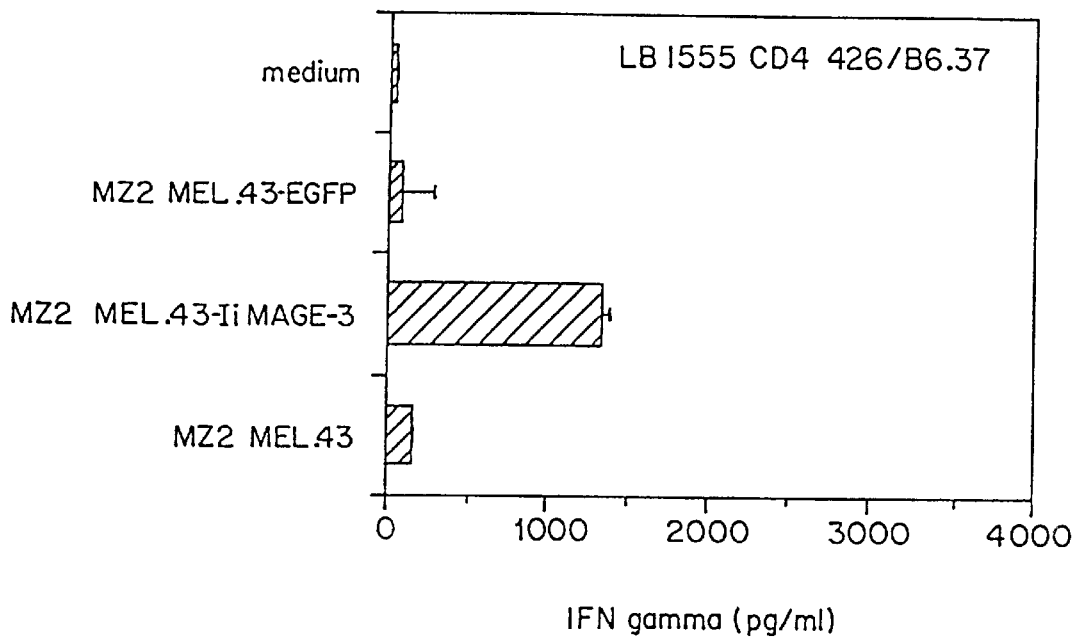
Figure 13B:
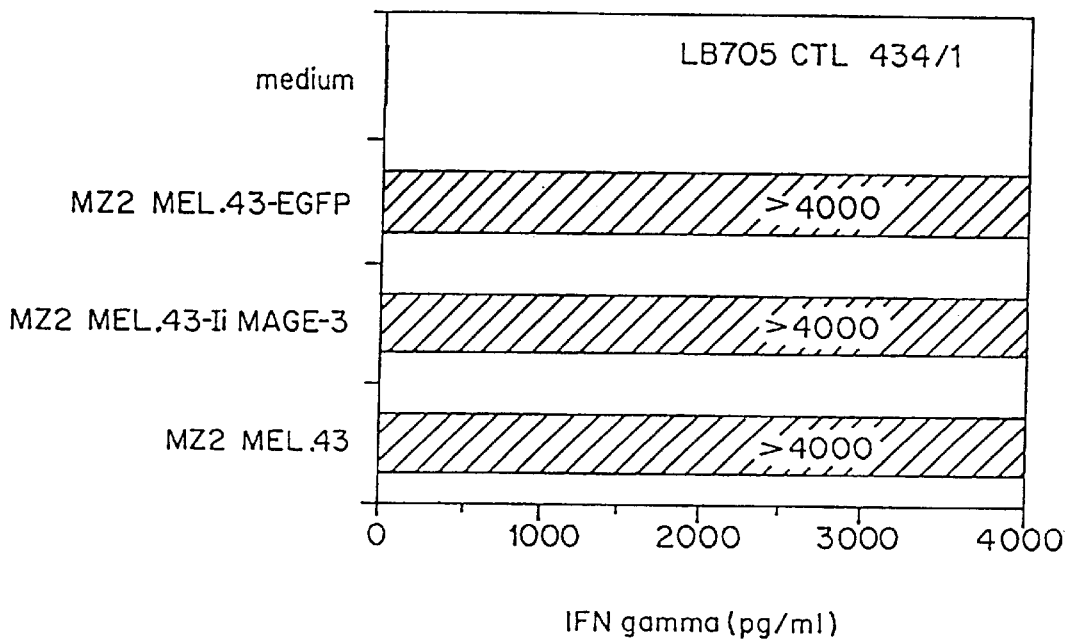

To further confirm to contribution of the Ii to presentation of MAGE-3 peptides in HLA class II molecules, the melanoma cell line MZ2-MEL.43 was transduced with MFG Ii MAGE-3 (MZ2-MEL.43-Ii MAGE-3) or with MFG EGFP (MZ2-MEL.43-EGFP). One month after transduction with MFG EGFP, 90% of MZ2-MEL.43 cells: expressed high levels of EGFP (not shown). MZ2-MEL.43 expresses the MAGE-3 protein endogenously, but does not present MAGE-3-derived peptides in HLA class II. However, after transduction of MZ2-MEL. 43 with MFG-Ii MAGE-3, it was recognized by the CD4 T cell clone LB1555 CD4 436/B6.37 after overnight coculture (FIG. 13A). INF-$\gamma$ release in the culture supernatant was measured by ELISA. This indicates that in contrast to the endogenously expressed MAGE-3, the Ii MAGE-3 can be processed for presentation in HLA class II. Both parental and transduced MZ2-MEL.43 activated the CTL clone LB705 CTL 434/1 (FIG. 13B).

Example 7

Two Other CD4$^+$ Clones Recognized a Second MAGE-3 Epitope

Figure 15A:
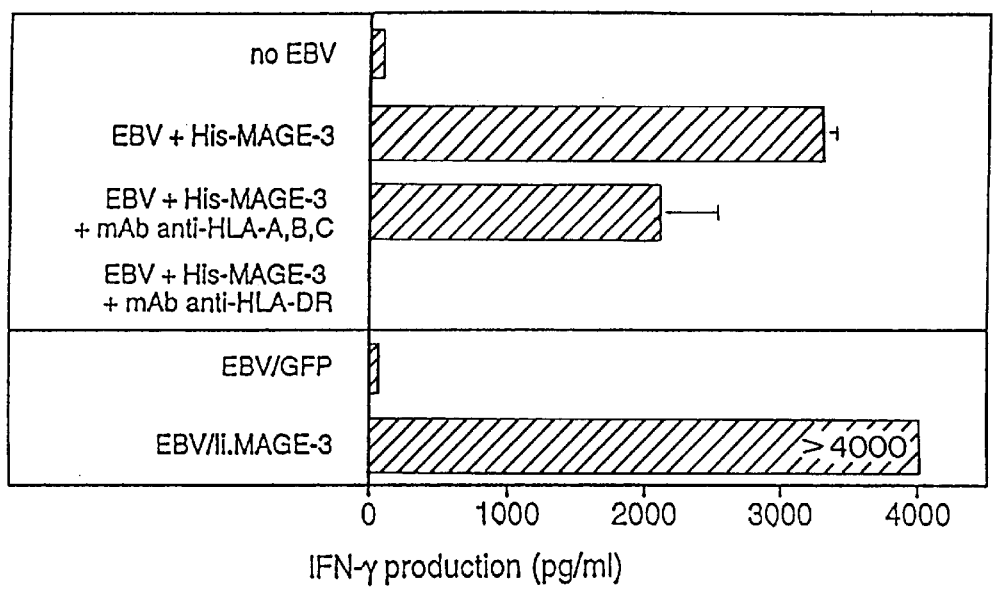

In order to confirm the efficacy of this protocol, dendritic cells. were fed with the MAGE-3 protein, using conditions described above, to stimulate autologous CD4$^+$ T lymphocytes from hemochromatosis patient LB1158 or from melanoma patient 7002. After four restimulations, the specific production of INF-$\gamma$ by an aliquot of each of the microcultures stimulated with the autologous EBV-B cells loaded with MAGE-3 were tested on day 35 for patient LBI 158 and day 37 for patient 7002. For each individual, one positive microculture was cloned using autologous EBV-B cells as stimulating cells, either retrotransduced with MFG Ii MAGE-3 for LB1158, or fed with protein MAGE-3 for patient 7002. LB1158 CD4$^+$ clone 22 and 7002 CD4$^+$ clone 2 were obtained. Both clones secreted INF-$\gamma$ upon stimulation with autologous EBV-B cells loaded with MAGE-3, or transduced with MFG Ii MAGE-3, which proves that the clones are specific for MAGE-3 and are not directed against a contaminant in the batch of protein. For clone 22, INF-γ release was inhibited by mAb 2B6 which recognizes HLA-DR molecules. Specifically, autologous EBV-B cells were incubated for 20 h in the presence of 20 μg/ml of recombinant His-MAGE-3 protein. Clone 22 (2500 cells) was incubated overnight with 5000 MAGE-3 loaded EBV-B cells in round botton microwells in the presence or absence of monoclonal antibodies which recognize HLA-A,B,C (W6/32) or HLA-DR (2B6). INF-γ secretion was measured after 20 h by ELISA (FIG. 15A).

Figure 15B:
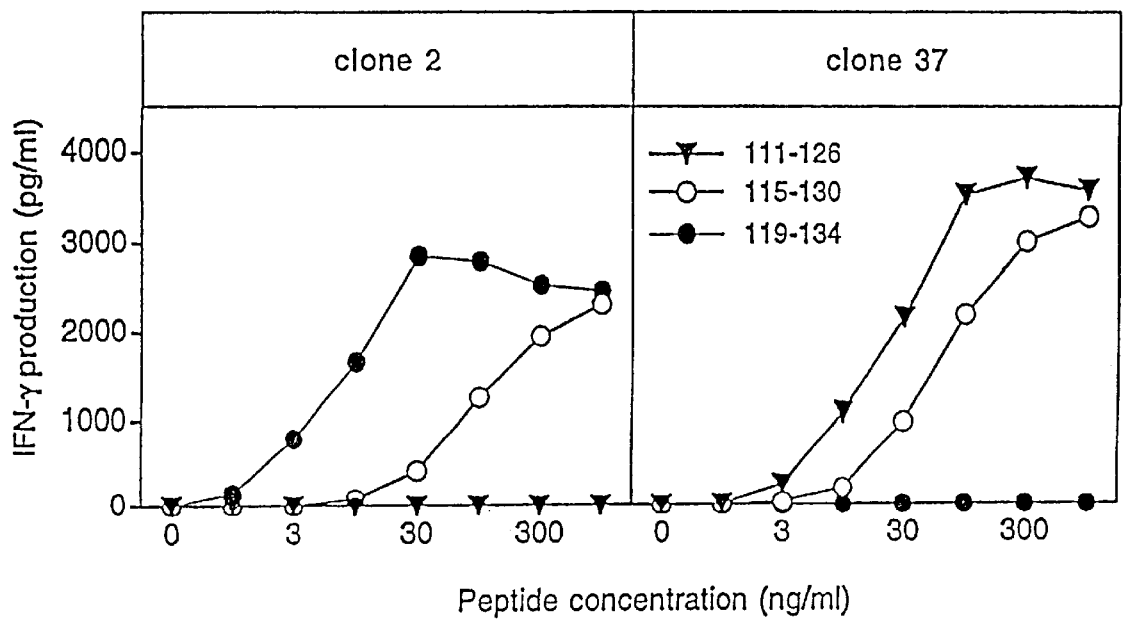

Peptides corresponding to parts of MAGE-3 (e.g., $MAGE_{107-122}$, $MAGE_{111-126}$, $MAGE_{115-130}$, $MAGE_{119-134}$) were tested for recognition by clone 2 and 22. HLA-DR13 EBV-B cells were pulsed for 2 h with different concentrations of these peptides. Clones 2 and 37 (2500 cells) were incubated with 5000 peptide pulsed cells in round-bottomed microwells for 20 h and assayed for INF-γ production. Peptide $MAGE-3_{119-134}$ (FLLLKYRAREPVTKAE; SEQ ID NO:23) scored positive. It stimulated secretion of INF-γ by clone 2 at a concentration of 10 ng/ml, whereas clone 37 was not stimulated by this peptide in the same conditions (FIG. 15B). Clone 22 was also stimulated by peptide $MAGE-3_{119-134}$ (SEQ ID NO:23) in similar experiments.

Donor LB1158 expresses the DRB1*0101, DRB1*1301 and DRB3*0202 alleles, whereas patient 7002 expresses the DRB1*0101, DRB1*1302 and DRB3*0301 A number of additional EBV-B cell lines were tested, which revealed that only those expressing DR13 were able to present the peptide to clone 2 and 22 (Table III). Autologous or allogeneic EBV-B cells were pulsed for 2 h with 1 μg/ml $MAGE-3_{119-134}$ peptide, and then washed. Clones 2 or 22 were incubated with 5000 peptide-pulsed EBV-B cells in round-bottomed microwells for 20 h and the clones' reactivity to the EBV-B cells was measured by ELISA as INF-γ secretion. Experiments were performed in triplicate.

TABLE III

| | IFN-γ production (pg/ml) after stimulation with peptide $MAGE-3_{119-134}$ of | |
|---|---|---|
| EBV-B cell line | clone 22 | clone 2 |
| DR13 positive | | |
| 7002 | >4000 | >4000 |
| LB1118 | 1345 | >4000 |
| LB1158 | 3967 | >4000 |
| LB1622 | 1250 | 3993 |
| LB1859 | >4000 | >4000 |
| LB1861 | 3865 | >4000 |
| LB1869 | >4000 | >4000 |
| MZ2 | 2030 | >4000 |
| OMW | 3651 | 3153 |
| DR13 negative | | |
| BM16 | 7 | 12 |
| BOB | 46 | 59 |
| BOLETH | 6 | 0 |
| LKT3 | 0 | 0 |
| OLGA | 6 | 0 |
| RML | 0 | 0 |
| RSH | 0 | 0 |
| TAB089 | 0 | 0 |
| TISI | 4 | 4 |

TABLE III-continued

| | IFN-γ production (pg/ml) after stimulation with peptide $MAGE-3_{119-134}$ of | |
|---|---|---|
| EBV-B cell line | clone 22 | clone 2 |
| VAF | 49 | 0 |
| VET | 56 | 0 |

Example 8

Definition of Minimal MAGE-3 Antigenic Peptides

Unlike HLA-class I-restricted peptides, class II-restricted peptides usually vary in length and tolerate extensions at both the amino and carboxy termini, because they are not fixed by their ends in the groove. It is therefore difficult to define precisely the length of the antigenic peptide. Therefore a large number of MAGE-3 peptides were tested at different concentrations (Tables IV and V). As shown in Table IV, autologous LB1555 EBV-B cells were incubated for 2 h with different MAGE-3 peptides. 2500 cells of clone 37 were then cocultured for 20 h in round-bottomed microwells with 5000 peptide-pulsed cells. INF-γ released in the supernatant of the cocultures was measured in an ELISA assay. The experiments were performed in triplicate. As shown in Table V, HLA-DR13 EBV-B cells were incubated for 2 h with different MAGE-3 peptides. Clones 2 and 22 (2500 cells) were then cocultured for 20 h in round-bottomed microwells with 5000 peptide-pulsed cells. INF-γ released in the supernatant of the cocultures was measured in an ELISA assay. The experiments was performed twice in duplicates. From these experiments it was concluded that a short peptide well recognized by clone 37 was AELVH-FLLLKYRAR ($MAGE-3_{114-127}$; SEQ ID NO:28) whereas short peptides well recognized by clone 2 and 22 were FLLLKYRAREPVT ($MAGE-3_{119-131}$; SEQ ID NO:34) and LLKYRAREPVTKAE ($MAGE-3_{121-134}$; SEQ ID NO:38).

As for HLA-class I-restricted peptides, HLA-class II-restricted peptides have preferred anchor residues within a HLA binding core of 9 to 10 amino acids. Most peptides binding to HLA-DRB1*1301 and B1*1302 are characterized by an I; L or V at the P1 position in the binding core; a L, V, M, A, W or Y at the P4 position; a R or K at the P6 position and a Y, F, A, S or T at the P9 or 10 position (Rammensee et al., *MHC Ligands and Peptide Motifs*, Molecular Biology Intelligence Unit, Springer, 1997). The foregoing results suggest that for the first antigenic peptide (recognized by clone 37), the 10 amino acids peptide LVH-FLLLKYR ($MAGE-3_{116-125}$; SEQ ID NO:41) is the binding core for HLA-DR13, L116 and Y125 residues serving respectively as P1 and P9/10 anchors (Table IV). Alternatively, for clone 37 recognition the 10 amino acid peptide VHFLLLKYRA ($MAGE-3_{117-126}$; SEQ ID NO:11) can be the binding core for. HLA-DR13, with V17 and A126 serving respectively as P1 and P9 anchors. For the second antigenic peptide (recognized by clone 2 and 22), the results suggest that the 10 amino acids peptide LKYRAREPVT ($MAGE-3_{122-131}$; SEQ ID NO:42) is the binding core for HLA-DR13, with residues L122, R127, and T131 serving respectively as P1, P6 and P10 anchors (Table V). Thus the peptides described herein for binding clones 37, 2 or 22 are encoded by nucleic acids which include the nucleotide sequences GTTCATTTC TGCTCCTCAA GTATCGAGCC (SEQ ID NO:13) or TTGGTTCATT TTCTGCTCCT CAAGTATCGA (SEQ ID NO:43) for clone 37, and CTCAAGTATC GAGCCAGGGA GCCGGTCACA (SEQ ID NO:44), for clones 2 or 22.

TABLE IV

| Peptide | peptide concentration (ng/ml) | | | | | | |
|---|---|---|---|---|---|---|---|
| | 1000 | 300 | 100 | 30 | 10 | 3 | 1 |
| | IFN-γ production (pg/ml) by clone 37 | | | | | | |
| VAELVHFLLLKYRARE | >4000 | >4000 | >4000 | 1647 | 376 | 300 | 30 |
| VAELVHFLLLKYRAR | >4000 | >4000 | >4000 | 2963 | 779 | 262 | 146 |
| VAELVHFLLLKYRA | >4000 | >4000 | 2534 | 648 | 87 | 179 | 7 |
| AELVHFLLLKYRARE | >4000 | >4000 | 3837 | 1473 | 235 | 230 | 38 |
| AELVHFLLLKYRAR | >4000 | >4000 | >4000 | 2862 | 802 | 272 | 151 |
| AELVHFLLLKYRA | >4000 | >4000 | >4000 | 2523 | 620 | 139 | 134 |
| ELVHFLLLKYRARE | >4000 | >4000 | 3095 | 1087 | 166 | 160 | 25 |
| ELVHFLLLKYRAR | >4000 | >4000 | 3633 | 1899 | 333 | 192 | 47 |

TABLE V

| Sequence | Peptide concentration (ng/ml) | | | | | | |
|---|---|---|---|---|---|---|---|
| | 1000 | 300 | 100 | 30 | 10 | 3 | 1 |
| | IFN-γ production (pg/ml) by clone 22 | | | | | | |
| FLLLKYRAREPVTKA | 2180 | 1965 | 1854 | 1775 | 1619 | 1294 | 283 |
| FLLLKYRAREPVTK | 453 | 115 | 28 | 10 | 1 | 0 | 0 |
| FLLLKYRAREPVT | 2183 | 1834 | 1510 | 1635 | 1099 | 584 | 291 |
| FLLLKYRAREPV | 1353 | 746 | 383 | 132 | 13 | 3 | 0 |
| FLLLKYRAREP | 30 | 7 | 6 | 7 | 1 | 0 | 0 |
| LLLKYRAREPVTKAE | 2214 | 1739 | 1679 | 1832 | 1440 | 965 | 718 |
| LLKYRAREPVTKAE | 2225 | 1826 | 1736 | 1651 | 1073 | 638 | 262 |
| LKYRAREPVTKAE | 2004 | 1475 | 1029 | 567 | 223 | 25 | 0 |
| KYRAREPVTKAE | 542 | 135 | 16 | 5 | 0 | 5 | 0 |
| | IFN-γ production (pg/ml) by clone 2 | | | | | | |
| FLLLKYRAREPVTKA | 3314 | 3354 | 2871 | 2713 | 1753 | 865 | 245 |
| FLLLKYRAREPVTK | 0 | 0 | 85 | 0 | 0 | 0 | 0 |
| FLLLKYRAREPVT | 3079 | 2860 | 2951 | 2003 | 1437 | 370 | 114 |
| FLLLKYRAREPV | 2667 | 1632 | 821 | 216 | 78 | 4 | 0 |
| FLLLKYRAREP | 23 | 0 | 85 | 0 | 0 | 0 | 0 |
| LLLKYRAREPVTKAE | 3033 | 3124 | 2857 | 2532 | 2028 | 639 | 169 |
| LLKYRAREPVTKAE | 3078 | 3186 | 2918 | 2012 | 1419 | 303 | 40 |
| LKYRAREPVTKAE | 2755 | 2544 | 1324 | 386 | 79 | 0 | 0 |
| KYRAREPVTKAE | 50 | 0 | 0 | 0 | 0 | 0 | 0 |

TABLE VI

| SEQ ID NO | PEPTIDE SEQUENCE |
|---|---|
| 24 | VAELVHFLLLKYRARE |
| 25 | VAELVHFLLLKYRAR |
| 26 | VAELVHFLLLKYRA |
| 27 | AELVHFLLLKYRARE |
| 28 | AELVHFLLLKYRAR |
| 29 | AELVHFLLLKYRA |
| 30 | ELVHFLLLKYRARE |
| 31 | ELVHFLLLKYRAR |
| 32 | FLLLKYRAREPVTKA |
| 33 | FLLLKYRAREPVTK |
| 34 | FLLLKYRAREPVT |
| 35 | FLLLKYRAREPV |
| 36 | FLLLKYRAREP |
| 37 | LLLKYRAREPVTKAE |
| 38 | LLKYRAREPVTKAE |
| 39 | LKYRAREPVTKAE |
| 40 | KYRAREPVTKAE |

Example 9

Recognition of Other MAGE Proteins by Clones 2 and 22

The peptide MAGE-3$_{119-134}$ (FLLLKYRAREPVTKAE; SEQ ID NO:23) is present identically in the amino acid sequences of MAGE-1 (amino acids 112–127), MAGE-2 (amino acids 119–134) and MAGE-6 (amino acids 119–134). Clones 2 and 22, but not clone 37, were stimulated by autologous EBV-B cells loaded with a MAGE-1 recombinant protein according to the assays described above. Thus, one of the two MAGE-3.DR13 epitopes may be useful for clinical trials with other MAGE products.

Homologous peptide sequences are found in other cancer antigens including MAGE-4, MAGE-8, MAGE-9, MAGE-10, MAGE-12, MAGE-B2, MAGE-C1. To determine if the CD4$^+$ T cell clones recognize these additional cancer associated antigens, the recombinant proteins, or synthesized peptides corresponding to the homologous region in these proteins, are used to load antigen presenting cells (such as EBV-B cells) to test for recognition by clone 2 or clone 22 according to the assays described above. Homologous peptide which are recognized by clone 2 or clone 22 may be regarded as functional variants of the MAGE-3 peptides described herein.

Other aspects of the invention will be clear to the skilled artisan and need not be repeated here. Each reference cited herein is incorporated by reference in its entirety.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An isolated nucleic acid molecule encoding a MAGE-3 HLA class II-binding peptide comprising a fragment of the amino acid sequence of SEQ ID NO:2 which binds an HLA class II molecule, or a functional variant thereof comprising one or more amino acid additions, substitutions or deletions.

2. The isolated nucleic acid of claim 1, wherein the nucleic acid comprises a nucleotide sequence selected from the group consisting of SEQ ID NO:13, SEQ ID NO:43 and SEQ ID NO:44.

3. The isolated nucleic acid molecule of claim 1, wherein the MAGE-3 HLA class II-binding peptide comprises an amino acid sequence selected from the group consisting of SEQ ID NO:11, SEQ ID NO:41 and SEQ ID NO:42, or a functional variant thereof.

4. The isolated nucleic acid molecule of claim 3, wherein the MAGE-3 HLA class II-binding peptide comprises an amino acid sequence selected from the group consisting of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39.

5. The isolated nucleic acid molecule of claim 3, wherein the MAGE-3 HLA class II-binding peptide consists of an amino acid sequence selected from the group consisting of SEQ ID NO:3, SEQ ID NO:4, SEQ ID NO:9, SEQ ID NO:10, SEQ ID NO:11, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:23, SEQ ID NO:32, SEQ ID NO:34, SEQ ID NO:35, SEQ ID NO:37, SEQ ID NO:38 and SEQ ID NO:39.

6. The isolated nucleic acid molecule of claim 1, further encoding an endosomal targeting signal.

7. An expression vector comprising the isolated nucleic acid of claim 1 operably linked to a promoter.

8. The expression vector of claim 7 wherein the nucleic acid comprises a nucleotide sequence selected from the group consisting of SEQ ID NO:13, SEQ ID NO:43 and SEQ ID NO:44.

9. The expression vector of claim 7 further comprising a nucleic acid which encodes an HLA-DRB1/13 molecule.

10. The expression vector of claim 8 further comprising a nucleic acid which encodes an HLA-DRB1/13 molecule.

11. A host cell transfected or transformed with the expression vector of claim 7.

12. A host cell transfected or transformed with the expression vector of claim 7, wherein the host cell expresses an HLA-DRB1/13 molecule.

13. A host cell transfected or transformed with the expression vector of claim 8.

14. A host cell transfected or transformed with the expression vector of claim 8, wherein the host cell expresses an HLA-DRB1/13 molecule.

15. A host cell transfected or transformed with the expression vector of claim 9.

16. A host cell transfected or transformed with the expression vector of claim 10.

* * * * *

UNITED STATES PATENT AND TRADEMARK OFFICE
CERTIFICATE OF CORRECTION

PATENT NO. : 6,426,217 B1 Page 1 of 1
APPLICATION NO. : 09/697884
DATED : July 30, 2002
INVENTOR(S) : Chaux et al.

It is certified that error appears in the above-identified patent and that said Letters Patent is hereby corrected as shown below:

On Title page
Item 75
inventor name "Jurgen Kurthals" should read --Jurgen Corthals--

Signed and Sealed this

Second Day of October, 2007

JON W. DUDAS
*Director of the United States Patent and Trademark Office*